US008486408B2

(12) United States Patent
Hossain et al.

(10) Patent No.: US 8,486,408 B2
(45) Date of Patent: Jul. 16, 2013

(54) METHODS FOR THE TREATMENT OF GRAFT-VERSUS-HOST DISEASE

(75) Inventors: Mohammad S. Hossain, Norcross, GA (US); Andrew T. Gewitz, Smyrna, GA (US); John D. Roback, Smyrna, GA (US); Edmund K. Waller, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 13/121,016

(22) PCT Filed: Oct. 2, 2009

(86) PCT No.: PCT/US2009/059437
§ 371 (c)(1),
(2), (4) Date: Apr. 19, 2011

(87) PCT Pub. No.: WO2010/040096
PCT Pub. Date: Apr. 8, 2010

(65) Prior Publication Data
US 2011/0206699 A1 Aug. 25, 2011

Related U.S. Application Data

(60) Provisional application No. 61/102,648, filed on Oct. 3, 2008.

(51) Int. Cl.
*A61K 35/28* (2006.01)
*A61K 39/085* (2006.01)
(52) U.S. Cl.
USPC .................. 424/172.1; 424/234.1; 424/258.1
(58) Field of Classification Search
None
See application file for complete search history.

(56) References Cited

U.S. PATENT DOCUMENTS

| | | | |
|---|---|---|---|
| 4,886,748 A | 12/1989 | Asaka et al. | |
| 5,618,533 A | 4/1997 | Flavell et al. | |
| 5,888,810 A | 3/1999 | Meinersmann et al. | |
| 6,130,082 A | 10/2000 | Majarian et al. | |
| 6,585,980 B1 | 7/2003 | Chan et al. | |
| 2003/0044429 A1 | 3/2003 | Aderem et al. | |
| 2005/0163764 A1 | 7/2005 | Medzhitov et al. | |

FOREIGN PATENT DOCUMENTS

| | | |
|---|---|---|
| WO | 02085933 A1 | 10/2002 |
| WO | WO 02/085933 * | 10/2002 |
| WO | 2005030133 A2 | 4/2005 |
| WO | 2007103048 A2 | 9/2007 |

OTHER PUBLICATIONS

Hayashi et al, Nature, 2001, vol. 410, pp. 1099-1103.*
Caron et al. The Journal of immunology, 2005, vol. 175, pp. 1551-1557.*
Zhang et al. The Journal of Immunology, 2007, vol. 179, pp. 3305-3314.*
Lazar et al. Mol. Cell. Biol., 1988, vol. 8, pp. 1247-1252.*
Wells, 1990, Biochemistry 29:8509-8517.*
Alegre et al., (2008), "The Multiple Facets of Toll-Like Receptors in Transplantation Biology.", Transplantation, 86(1): 1-9.
Burdelya et al., (2008), "An Agonist of Toll-Like Receptor 5 Has Radioprotective Activity in Mouse and Primate Models.", Science 320(5873): 226-230.
Donnelly et al., (2002), "Two Nonadjacent Regions in Enteroaggregative *Escherichia coli* Flagellin Are Required for Activation of Toll-like Receptor 5.", Journal of Biological Chemistry, 277(43): 40456-40461.
Eaves-Pyles et al., (2001), "*Salmonella* Flagellin-Dependent Proinflammatory Responses Are Localized to the Conserved Amino and Carboxyl Regions of the Protein.", The Journal of Immunology, 167(12): 7009-7016.
Genbank Accession No. AAN74969, Dec. 1, 2002.
Genbank Accession No. BAB59884, May 19, 2007.
Genbank Accession No. BAC44986, Dec. 1, 2002.
Genbank Accession No. CAA02137, Jun. 20, 1996.
Genbank Accession No. CAL35450, Aug. 18, 2011.
Genbank Accession No. NP_003259, Nov. 25, 2012.
Genbank Accession No. YP_001217666, Sep. 10, 2012.
Gill et al., (1983), "The nucleotide sequence of the Mr = 28,500 flagellin gene of Caulobacter crescentus.", Journal of Biological Chemistry, 258(12): 7395-7401.
Hayashi et al., (2001), "The innate immune response to bacterial flagellin is mediated by Toll-like receptor 5.", Nature, 410(6832): 1099-1103.
Hossain et al., (2011), "Flagellin, a TLR5 Agonist, Reduces Graft-versus-Host Disease in Allogeneic Hematopoietic Stem Cell Transplantation Recipients While Enhancing Antiviral Immunity.", The Journal of Immunology, 187(10): 5130-5140.
Korngold et al., (1983), "Lethal GVHD Across Minor Histocompatibility Barriers: Nature of the Effector Cells and Role of the H-2 Complex.", Immunological Reviews, 71(1): 5-30.
Kuwajima et al., (1986), "Nucleotide sequence of the hag gene encoding flagellin of *Escherichia coli*.", Journal of Bacteriology, 168(3): 1479-1483.

(Continued)

*Primary Examiner* — Bridget E Bunner
*Assistant Examiner* — Fozia Hamud
(74) *Attorney, Agent, or Firm* — Emory Patent Group; James C. Mason; Susanne Hollinger

(57) ABSTRACT

Methods are disclosed for treating or preventing graft versus host disease in a subject. The methods include selecting a subject in need of treatment for graft versus host disease; and administering to the subject a therapeutically effective amount of a TLR5 agonist such as a flagellin polypeptide, or a polynucleotide encoding the flagellin, thereby treating or preventing graft versus host disease in the subject. Methods are also disclosed for reducing susceptibility to an opportunistic infection in a subject who is a bone marrow transplant recipient. The methods include selecting a subject who has had a bone marrow or hematopoietic stem cell transplant; and administering to the subject a therapeutically effective amount of a TLR5 agonist such as a flagellin polypeptide or a polynucleotide encoding the polypeptide, and administering to the subject an effective amount antigen of the opportunistic infection, thereby reducing the susceptibility to the opportunistic infection in the subject.

14 Claims, 8 Drawing Sheets

OTHER PUBLICATIONS

Liaudet et al., (2002), "The Flagellin-TLR5 Axis: Therapeutic Opportunities.", Drug News Perspect, 15(7): 397-409.

Lombardo, E., (2008), "Toll-like receptor signaling: Involvement in graft transplantation.", Inmunologia, 27(2): 69-77.

McSorley et al., (2002), "Bacterial Flagellin Is an Effective Adjuvant for CD4+ T Cells In Vivo.", The Journal of Immunology, 169(7): 3914-3919.

Mimori-Kiyosue et al., (1997), "Locations of terminal segments of flagellin in the filament structure and their roles in polymerization and polymorphism.", Journal of Molecular Biology, 270(2): 222-237.

Murthy et al., (2004), "Identification of Conserved Domains in *Salmonella* muenchen Flagellin That Are Essential for Its Ability to Activate TLR5 and to Induce an Inflammatory Response in Vitro.", Journal of Biological Chemistry, 279(7): 5667-5675.

Samatey et al., (2001), "Structure of the bacterial flagellar protofilament and implications for a switch for supercoiling.", Nature, 410(6826): 331-337.

Schoenhals et al., (1993), "Comparative analysis of flagellin sequences from *Escherichia coli* strains possessing serologically distinct flagellar filaments with a shared complex surface pattern.", Journal of Bacteriology, 175(17): 5395-5402.

Smith et al., (2003), "Toll-like receptor 5 recognizes a conserved site on flagellin required for protofilament formation and bacterial motility.", Nat Immunol, 4(12): 1247-1253.

Tino, T., (1977), "Genetics of Structure and Function of Bacterial Flagella.", Annual Review of Genetics 11(1): 161-182.

Verma et al., (2005), "Roles of Specific Amino Acids in the N Terminus of Pseudomonas aeruginosa Flagellin and of Flagellin Glycosylation in the Innate Immune Response.", Infection and Immunity, 73(12): 8237-8246.

Wei et al., (1985), "Covalent structure of three phase-1 flagellar filament proteins of *Salmonella*.", Journal of Molecular Biology, 186(4): 791-803.

* cited by examiner

FIG. 2: Experimental Design to use flagellin

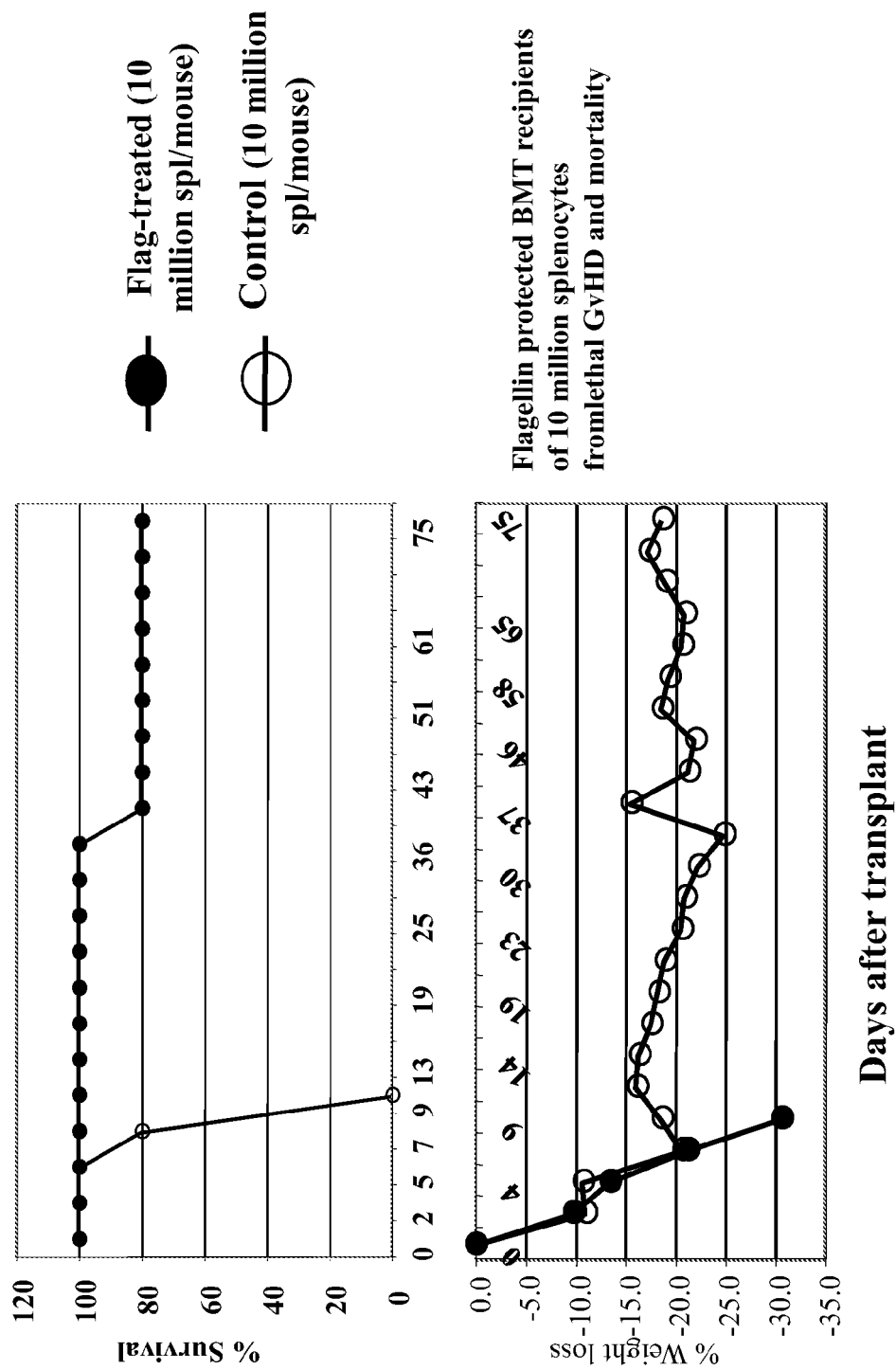

METHODS FOR THE TREATMENT OF GRAFT-VERSUS-HOST DISEASE

PRIORITY CLAIM

This claims the benefit of U.S. Provisional Application No. 61/102,648, filed Oct. 3, 2009, which is incorporated by reference herein in its entirety.

STATEMENT OF GOVERNMENT SUPPORT

This invention was made with United States government support pursuant to grant ROI CA 74364-04 from the National Cancer Institute, National Institutes of Health; the United States government has certain rights in the invention.

FIELD

This application relates to the field of graft versus host disease, specifically to the use of a TLR5 agonist, such as flagellin, to prevent or treat graft versus host disease.

BACKGROUND

Graft versus host disease ("GVHD") is a sometimes fatal, often debilitating complication that arises in patients who have received allogeneic bone marrow transplants. Marrow transplants become necessary in the treatment of certain diseases, such as leukemia, aplastic anemia or certain genetic disorders, in which the patient's own marrow is severely flawed and where total body irradiation or chemotherapy destroy the patient's hematopoietic system. Absent reconstitution of the hematopoietic system, the patient will be severely immunosuppressed and susceptible to infection. In addition, the donor immune system that engrafts in the host may recognize the host as "foreign" and initiate GVHD, an anti-host immunological attack. Hence GVHD is frequently encountered in bone marrow transplantation and presents a major obstacle to the successful treatment of the above disorders.

Working with the H2 histocompatability system of mice, Korngold and Sprent, Immunological Rev., 71:5 (1983), have reviewed the suspected etiology and pathology of GVHD. Briefly, in its acute form, GVHD is an extraordinarily morbid and often fatal disorder which is primarily, if not exclusively, mediated by T lymphocytes. It typically results from the incomplete immunologic matching of donor with recipient Human Leukocyte antigens (HLA). There are four major HLA antigens: the Class I HLA-A, HLA-B and HLA-C antigens; and the Class II HLA-D region antigens. These antigens form the major histocompatability complex (MHC), and are expressed in virtually all cells, including nucleated cells in the bone marrow. MHC antigens are cell surface glycoproteins expressed on the lipid membrane. These HLA antigens can trigger the immune system (principally T cells) to respond to foreign antigens. For a more detailed description of the HLA system, see P. Weisz-Carrington, Principles of Clinical Immunohematology, p. 218, YearBook Medical Publishers, Inc. (1986).

Even in those cases where the most complete HLA matching is correctly done, GVHD can result. It has been suggested that GVHD results, in those instance, from alloaggression due to minor histocompatibility antigen differences for which many authors have suggested the depletion of donor T cells as a means to avoid GVHD. Various immunosuppressive agents have been employed for the treatment of GVHD. Currently, allograft rejection is controlled using immunosuppressive agents such as cyclosporin A, azathioprine, corticosteroids including prednisone, and methylprednisolone, cyclophosphamide, and FK506. Cyclosporin A, the most powerful and most frequently used immunosuppressant, revolutionized the field of organ transplant surgery. Other immunosuppressive agents such as FK506, rapamycin, mycophenolic acid, 15-deoxyspergualin, mimoribine, misoprostol, OKT3 and anti-IL-2 receptor antibodies, have been used in the treatment and/or prevention of organ transplantation rejection (Briggs, Immunology letters, 29 (1-2), 89 94, 1991; FASEB 3:3411, 1989). Although the development of new immunosuppressive drugs has led to substantial improvement in the survival of patients, these drugs are associated with a high incidence of side effects such as nephrotoxicity and/or hepatotoxicity. Thus, a need remains for new agents for the treatment of GVHD.

SUMMARY

It is disclosed herein that a TLR5 agonist, such as flagellin polypeptide, or a polynucleotide encoding the polypeptide, can be used in the treatment of graft versus host disease (GVHD). It is also disclosed that a TLR5 agonist, such as flagellin can be used to treat opportunistic infections in subjects who have received a bone marrow transplant.

In some embodiments, methods are disclosed for treating or preventing graft versus host disease in a subject. The methods include selecting a subject in need of treatment for graft versus host disease; and administering to the subject a therapeutically effective amount of a TLR5 agonist, such as a flagellin polypeptide, or a polynucleotide encoding the flagellin polypeptide, thereby treating or preventing graft versus host disease in the subject. In some examples, the subject is an allogeneic bone marrow transplant recipient or an allogeneic or autologous hematopoietic stem cell transplant recipient.

In additional embodiments, methods are also disclosed for reducing susceptibility to an opportunistic infection in a subject who is a bone marrow transplant recipient. The methods include selecting a subject who has had a bone marrow transplant, such as an allogeneic bone marrow transplant, or hematopoietic stem cell transplant; and administering to the subject a therapeutically effective amount of a flagellin polypeptide or a polynucleotide encoding the polypeptide. The method also includes administering to the subject an effective amount of antigen of the opportunistic infection, thereby reducing the susceptibility to the opportunistic infection in the subject.

The foregoing and other features and advantages will become more apparent from the following detailed description of several embodiments, which proceeds with reference to the accompanying figures.

BRIEF DESCRIPTION OF THE FIGURES

FIG. 8 is a graph showing that flagellin protected HSCT recipients from lethal GVHD (monitored as weight loss) and the associated mortality. CB6F1 mice were injected i.p. with 50 micrograms of flagellin, and then were irradiated (5.5 Gy) 3 and 6 hours later for myeloablation (5.5 Gy each dose). Twenty-four hours after the flagellin injection, mice were transplanted by i.v. infusion of 5×10$^6$ bone marrow cells (T-cell depleted) and 10×10$^6$ plastic non-adherent splenocytes. The transplanted cells were isolated from C57BL/6 donors same as described above (see FIG. 2). The HSCT recipients received a second i.p. injection of flagellin (50 μg/mouse) 24 hours after HSCT. Mice were longitudinally tracked to monitor weight loss (as a marker for GvHD) and survival. Filled circles indicate the weight loss and mortality of mice treated with flagellin; open circles indicate the weight loss and mortality of control HSCT recipient mice.

SEQUENCE LISTING

Figure 1:
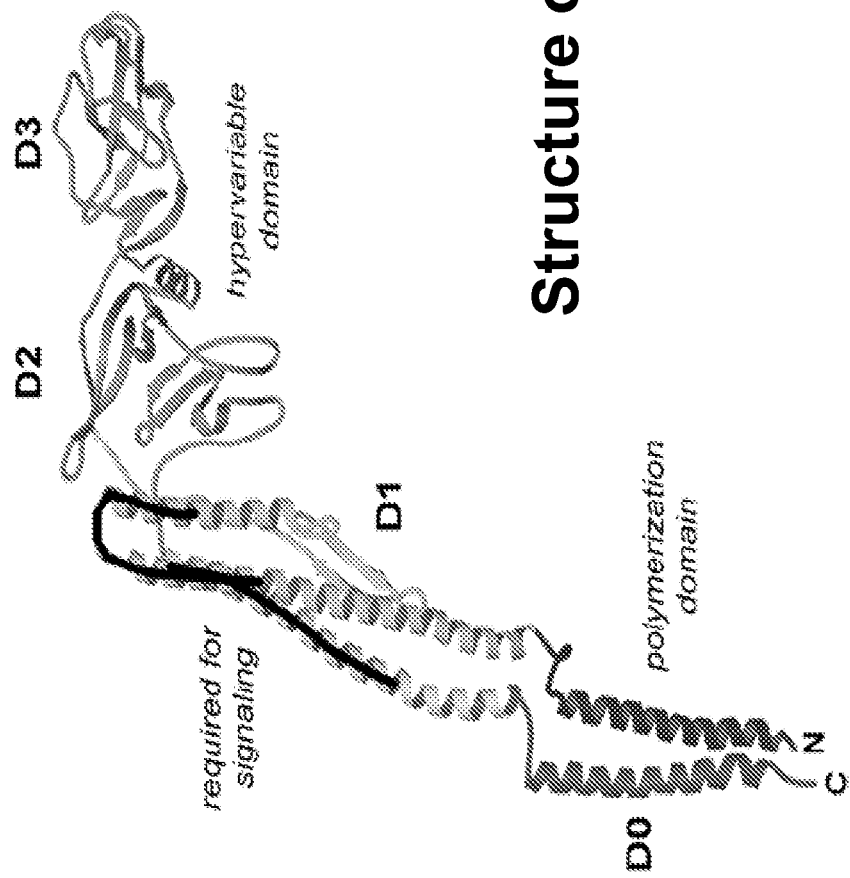
FIG. 1 is a schematic diagram of flagellin, a TLR5 agonist (molecular size 100-150 kDa). The D0, D1, D2 and D3 domains are shown, along with the location of the N-terminal and C-terminal regions for TLR5 signaling. The D0 domain consists of approximately 50 amino acid residues within the N- and C-termini, form the inner core of the flagellin protein and is responsible for flagellin's ability to polymerize into a filament. D1 domain is primarily alpha-helical and highly conserved region and is required for signaling. D2 and D3 are mostly beta-strand hypervariable domains and bind with the TLR5.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 and SEQ ID NO: 2 are exemplary amino acid sequences of flagellin.

SEQ ID NOs: 3-4 are the sequence of a flagellin polypeptide.

DETAILED DESCRIPTION

Methods for treating graft versus host disease are disclosed herein. Methods for treating an opportunistic infection in a subject who has had a bone marrow transplant, or a hematopoietic stem cell transplant, are also disclosed herein.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Antibody: A polypeptide ligand comprising at least a light chain or heavy chain immunoglobulin variable region which specifically recognizes and binds an epitope (e.g., an antigen, such as a tumor or viral antigen or a fragment thereof). This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (e.g., humanized murine antibodies), heteroconjugate antibodies (e.g., bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, an immunoglobulin has a heavy and light chain. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (e.g., see U.S. Pat. No. 5,585,089).

A "neutralizing antibody" is an antibody that interferes with any of the biological activities of a polypeptide, such as TLR-5. For example, a neutralizing antibody specifically binds TLR-5. In several examples, the neutralizing antibody can reduce TLR-5 activity by about 50%, about 70%, about 90% or more. Any standard assay to measure TLR activity, including those described herein, may be used to assess potentially neutralizing antibodies.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen, a uterine specific antigen, and/or a testes specific antigen. A tissue specific antigen may be expressed by more than one tissue, such as, but not limited to, an antigen that is expressed in more than one reproductive tissue, such as in both prostate and uterine tissue. A disease-specific antigen is expressed coincidentally with a disease process, and can be an antigen from an infectious agent, such as a bacteria, virus or fungus. Specific non-limiting examples of a disease-specific antigen are an antigen of cytomegalovirus, *Candida albicans*, human immunodeficiency virus, *Staphlococcus aureus*, *Steptococcus pyogenes*, *Pseudomas aeruginosa*, *Acinteobacter baumanni*, *Toxoplasma gondii*, *Pneumocystitis carinii*, or *Aspergillus*. A disease-specific antigen can be an antigen recognized by T cells or B cells.

Antigen-presenting cell (APC): A cell that can present antigen bound to MHC class I or class II molecules to T cells. APCs include, but are not limited to, monocytes, macrophages, dendritic cells, B cells, T cells and Langerhans cells. A T cell that can present antigen to other T cells (including CD4+ and/or CD8+ T cells) is an antigen presenting T cell (T-APC).

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule.

Encode: A polynucleotide is said to encode a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Expression: The process by which a gene's coded information is converted into the structures present and operating in the cell. Expressed genes include those that are transcribed into mRNA and then translated into protein and those that are transcribed into RNA but not translated into protein (for example, siRNA, transfer RNA and ribosomal RNA). Thus, expression of a target sequence, such as a gene or a promoter region of a gene, can result in the expression of an mRNA, a protein, or both. The expression of the target sequence can be inhibited or enhanced (decreased or increased).

Graft versus Host Disease (GVHD): A common complication of allogeneic bone marrow transplantation or hematopoietic stem cells transplantation in which functional immune cells in the transplanted marrow recognize the recipient as "foreign" and produce an immune response to the host tissue. According to the 1959 Billingham Criteria, there are three criteria must be met in order for GVHD to occur: 1) Administration of an immunocompetent graft, with viable and functional immune cells; 2) the recipient is immunologically histoincompatible; 3) The recipient is immunocompromised and therefore cannot destroy or inactivate the transplanted cells.

Clinically, graft-versus-host-disease is divided into acute and chronic forms. The acute or fulminant form of the disease (aGVHD) is normally observed within the first 100 days post-transplant, and is a major challenge to the effectiveness of transplants owing to the associated morbidity and mortality. The chronic form of graft-versus-host-disease (cGVHD) normally occurs after 100 days. The appearance of moderate to severe cases of cGVHD adversely influences long-term survival. After bone marrow transplantation, T cells present in the graft, either as contaminants or intentionally introduced into the host, attack the tissues of the transplant recipient after perceiving host tissues as antigenically foreign. The T cells produce an excess of cytokines, including TNF alpha and interferon-gamma (IFNγ). A wide range of host antigens can initiate graft-versus-host-disease, among them the human leukocyte antigens (HLAs). However, graft-versus-host-disease can occur even when HLA-identical siblings are the donors. Classically, acute graft-versus-host-disease is characterized by selective damage to the liver, skin and mucosa, and the gastrointestinal tract. Additional studies show that that other graft-versus-host-disease target organs include the immune system (such as the bone marrow and the thymus) itself, and the lungs in the form of idiopathic pneumonitis. Chronic graft-versus-host-disease also attacks the above organs, but over its long-term course can also cause damage to the connective tissue and exocrine glands.

Flagellin: The basic element of bacterial flagella; surface structures on bacteria, such as gram negative bacteria, involved in motility. In nature, flagellin has a molecular weight of approximately 40,000 daltons, and is composed of subunits arranged in several-stranded helix formation somewhat resembling myosin in structure. Exemplary flagellin proteins are described, for example, in U.S. Pat. Nos. 6,585,980; 6,130,082; 5,888,810; 5,618,533; and 4,886,748; U.S. Patent Publication No. US 2003/0044429 A1; and Donnelly et al., (2002) J. Biol. Chem. 43: 40456, all incorporated herein by reference. In nature, flagellin includes (i) a flagellin N-terminal constant region; and (ii) a flagellin C-terminal constant region and (iii) a flagellin hypervariable region between the constant regions.

Hematopoietic Stem Cells: Stem cells that give rise to all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells). hematopoietic stem cells are identified by their small size, lack of lineage (lin) markers, low staining (side population) with vital dyes such as rhodamine 123 (rhodamine$^{DULL}$, also called rho$^{lo}$) or Hoechst 33342, and presence of various antigenic markers on their surface, many of which belong to the cluster of differentiation series, for example: CD34, CD38, CD90, CD133, CD105, CD45 and c-kit. Hematopoietic stem cells are negative for the markers that are used for detection of lineage commitment, and are, thus, called Lin−; and, during their purification by fluorescent activated cell sorting (FACS). Lineage markers are different mature blood-lineage marker, such as CD13 and CD33 for myeloid cells, CD71 for erythroid cells, CD19 for B cells, CD61 for megakaryocytic cells. Lineage markers in mice include B220 (murine CD45) for B cells, Mac-1 (CD11b/CD18) for monocytes, Gr-1 for Granulocytes, Ter119 for erythroid cells, I17Ra, CD3, CD4, CD5, CD8 for T cells. In some embodiments antibodies are used as a mixture to deplete the lin+ cells or late multipotent progenitors (MPP)s from blood cells or bone marrow cells in order to purify hematopoietic stem cells. In one example, human hematopoietic stem cells are CD34$^{+}$, CD59$^{+}$, Thy1/CD90$^{+}$, CD38$^{lo/-}$, C-kit/CD117$^{+}$, lin$^{-}$. In another example, murine hematopoietic stem cells are CD34$^{lo/-}$, SCA-1$^{+}$, Thy1.1$^{+/lo}$, CD38$^{+}$, C-kit$^{+}$, lin$^{-}$.

Hematopoietic stem cell transplantation (HSCT) or bone marrow transplantation: The transplantation of blood stem cells derived from the bone marrow or blood. Most hematopoietic stem cell transplantation procedures are now performed using stem cells collected from the peripheral blood, rather than from the bone marrow. Generally, collecting peripheral blood stem cells provides a larger number of hematopoietic stem cells, does not require that the donor be subjected to general anesthesia to collect the graft, results in a shorter time to engraftment, and may provide for a lower long-term relapse rate.

Autologous HSCT involves isolation of hematopoietic stems cells (HSC) from the patient and storage of the harvested cells in a freezer. The patient is then treated with high-dose chemotherapy with or without radiotherapy in the form of total body irradiation to eradicate the patient's malignant cell population at the cost of also eliminating the patient's bone marrow stem cells, then return of the patient's own stored stem cells to their body. Autologous transplants have the advantage of a lower risk of graft rejection and infection, since the recovery of immune function is rapid. Also, the incidence of a patient experiencing graft-versus-host disease is close to none as the donor and recipient are the same individual. However, in malignant disease the likelihood of cancer relapse and related mortality is high relative to allogeneic HSCT.

Allogeneic HSCT involves two people: the (healthy) donor and the (patient) recipient. Allogeneic HSC donors must have a tissue (HLA) type that matches the recipient. Matching is performed on the basis of variability at three or more loci of the (HLA) gene, and a perfect match at these loci is preferred. Even if there is a good match at these critical alleles, the recipient will require immunosuppressive medications to mitigate graft-versus-host disease. Allogeneic transplant donors may be related (usually a closely HLA matched sibling) or unrelated (donor who is not related and found to have very close degree of HLA matching). Allogeneic transplants are also performed using umbilical cord blood as the source of stem cells. In general, by transplanting healthy stem cells to the recipient's immune system, allogeneic HCSTs appear to improve chances for cure or long-term remission once the immediate transplant-related complications are resolved.

The chemotherapy or irradiation given immediately prior to a transplant is called the conditioning or preparative regimen, the purpose of which is to help eradicate the patient's disease prior to the infusion of HSC and to suppress immune reactions. The bone marrow can be ablated with dose-levels that cause minimal injury to other tissues. In allogeneic transplants a combination of cyclophosphamide with busulfan or total body irradiation is commonly employed.

Heterologous: Originating from separate genetic sources or species. Generally, an antibody that specifically binds to a protein of interest will not specifically bind to a heterologous protein.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein (e.g. HLA-A02.01) and by their ability to stimulate CD4 and/or CD8 when presented in the context of the MHC protein.

Immunogenic composition: A composition comprising an immunogenic polypeptide or a nucleic acid encoding the immunogenic polypeptide that induces a measurable CTL response against cells expressing the polypeptide, or induces a measurable B cell response (such as production of antibodies that specifically bind the polypeptide) against the polypeptide. The immunogenic polypeptide can be an antigen of an opportunistic infection. For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and or immunogenic polypeptide, in pharmaceutically acceptable carriers, and/or other agents. An immunogenic composition can optionally include an adjuvant, a costimulatory molecule, or a nucleic acid encoding a costimulatory molecule. A polypeptide, or nucleic acid encoding the polypeptide, can be readily tested for its ability to induce a CTL or antibodies by art-recognized assays.

Inhibiting or treating a disease: Inhibiting a disease, such as graft versus host disease or an opportunistic infection, refers to inhibiting the full development of a disease, lessening the physiological effects of the disease process, or preventing the development of the disease. In several examples, inhibiting or treating a disease refers to lessening symptoms of graft versus host disease or an infection with a pathogen. In another embodiment, treatment of an infection can refer to inhibiting development, preventing, or lessening a symptom of the infection. "Treatment" refers to a therapeutic intervention that ameliorates a sign or symptom of a disease or pathological condition related to the disease. Therapeutic vaccination refers to administration of an agent to a subject already infected with a pathogen. In some embodiments, the subject can be asymptomatic, so that the treatment prevents the development of a symptom. The treatment, such as the administration of flagellin, can also reduce the severity of one or more existing symptoms, or reduce pathogen load.

Infectious disease: Any disease caused by an infectious agent. Examples of infectious pathogens include, but are not limited to: viruses, bacteria, mycoplasma and fungi. In a particular example, it is a disease caused by at least one type of infectious pathogen. In another example, it is a disease caused by at least two different types of infectious pathogens. Infectious diseases can affect any body system, be acute (short-acting) or chronic/persistent (long-acting), occur with or without fever, strike any age group, and overlap each other. Infectious diseases can be opportunistic infections, in that they occur more frequently in immunocompromised subjects Viral diseases commonly occur after immunosuppression due to re-activation of viruses already present in the recipient. Particular examples of viral infections include, but are not limited to, cytomegalovirus (CMV) pneumonia, enteritis and retinitis; Epstein-Barr virus (EBV) lymphoproliferative disease; chicken pox/shingles (caused by varicella zoster virus, VZV); HSV-1 and -2 mucositis; HSV-6 encephalitis, BK-virus hemorrhagic cystitis; viral influenza; pneumonia from respiratory syncytial virus (RSV); AIDS (caused by HIV); and hepatitis A, B or C. Opportunistic infections occur in a subject with a compromised immune system, such as a subject who has been immuno-depleted and recently received a bone marrow transplant or a hematopoietic stem cell transplant. These infections include, but are not limited to cytomegalovirus, *Candida albicans*, human immunodeficiency virus, *Staphlococcus aureus, Steptococcus pyogenes, Pseudomas aeruginosa, Acinteobacter baumanni, Toxoplasma gondii, Pneumocystitis carinii*, or *Aspergillus* infections.

Additional examples of infectious virus include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of fungal infections include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans.*

Examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira*, and *Actinomyces israelli*. Other infectious organisms (such as protists) include: *Plasmodium falciparum* and *Toxoplasma gondii*.

"Alleviating a symptom of an opportunistic infection" is ameliorating any condition or symptom associated with the infection. Alternatively, alleviating a symptom of a infection can involve reducing the infectious microbial (such as viral, bacterial, fungal or parasitic) load in the subject relative to such load in an untreated control. As compared with an equivalent untreated control, such reduction or degree of prevention is at least 5%, 10%, 20%, 40%, 50%, 60%, 80%, 90%, 95%, or 100% as measured by any standard technique. Desirably, the opportunistic infection is completely cleared as detected by any standard method known in the art, in which case the opportunistic infection. Diagnosis of an infection may be by any suitable means. Diagnosis and monitoring may involve, for example, detecting the level of microbial load in a biological sample (for example, a tissue biopsy, blood test, or urine test), detecting the level of a surrogate marker of the microbial infection in a biological sample, detecting symptoms associated with persistent infections, or detecting immune cells involved in the immune response typical of persistent infections (for example, detection of antigen specific T cells that are anergic and/or functionally impaired). A subject in whom the development of an infection is being prevented, and thus has been treated, may or may not have received such a diagnosis. One skilled in the art will understand that these subjects may have been subjected to the same standard tests as described above or may have been identified, without examination, as one at high risk due to the presence of one or more risk factors (such as receiving a bone marrow transplant or a hematopoietic stem cell transplant).

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

A "purified antibody" is at least 60%, by weight free from proteins and naturally occurring organic molecules with which it is naturally associated. In some examples the preparation is at least about 75%, at least about 80%, at least about 90%, at least about 95%, or at least about 99%, by weight of antibody, such as a TLR-5 specific antibody. A purified antibody can be obtained, for example, by affinity chromatography using recombinantly-produced protein or conserved motif peptides and standard techniques.

Label: A detectable compound or composition that is conjugated directly or indirectly to another molecule to facilitate detection of that molecule. Specific, non-limiting examples of labels include fluorescent tags, enzymatic linkages, and radioactive isotopes.

Lymphocytes: A type of white blood cell that is involved in the immune defenses of the body. There are two main types of lymphocytes: B cells and T cells.

Major Histocompatability Complex (MHC): A generic designation meant to encompass the histocompatability antigen systems described in different species, including the human leukocyte antigens ("HLA").

Mammal: This term includes both human and non-human mammals. Similarly, the term "subject" includes both human and veterinary subjects.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition or a cell to achieve a desired effect in a subject being treated. For instance, this can be the amount of flagellin polypeptide or a polynucleotide encoding the polypeptide, or a TLR5 agonist necessary to induce an immune response, treat prevent graft versus host disease or to measurably alter outward symptoms of a graft versus host disease or an opportunistic infection. When administered to a subject, a dosage will generally be used that will achieve target tissue concentrations (for example, in lymphocytes) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (e.g., glycosylation or phosphorylation). A polypeptide can be between 3 and 30 amino acids in length. In one embodiment, a polypeptide is from about 7 to about 25 amino acids in length. In yet another embodiment, a polypeptide is from about 8 to about 10 amino acids in length. In yet another embodiment, a peptide is about 9 amino acids in length. With regard to polypeptides, "comprises" indicates that additional amino acid sequence or other molecules can be included in the molecule, "consists essentially of" indicates that additional amino acid sequences are not included in the molecule, but that other agents (such as labels or chemical compounds) can be included, and "consists of" indicates that additional amino acid sequences and additional agents are not included in the molecule.

Specific binding agent: An agent that binds substantially only to a defined target. Thus TLR5 specific binding agent is an agent that binds substantially to a TLR5 polypeptide and not unrelated polypeptides. In one embodiment, the specific binding agent is a monoclonal or polyclonal antibody that specifically binds a TLR5 polypeptide.

The term "specifically binds" refers, with respect to an antigen such as TLR5, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. Specific binding results in a much stronger association between the antibody (or other ligand) and cells bearing the antigen than between the antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the TLR polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8+ T cell is a cytotoxic T lymphocyte. In another embodiment, a CD8+ cell is a suppressor T cell. A T cell is "activated" when it can respond to a specific antigen of interest presented on an antigen presenting cells.

Toll-like Receptor (TLR): A class of single membrane-spanning non-catalytic receptors that recognize structurally conserved molecules derived from microbes once they have breached physical barriers such as the skin or intestinal tract mucosa, and activate immune cell responses. They are believed to play a key role in the innate immune system. Thirteen TLRs (named simply TLR1 to TLR13) have been identified in humans and mice together, and equivalent forms of many of these have been found in other mammalian species. They recognize pathogen-associated molecular patterns (PAMPs) that are expressed on infectious agents, and mediate the production of cytokines necessary for the development of effective immunity.

Flagellin specifically binds TLR5. The activation of this receptor mobilizes the nuclear factor NF-kappaB and stimulates tumor necrosis factor-alpha production. An exemplary amino acid sequence for human TLR5 can be found as GEN-BANK® Accession No. NP_003259, which is incorporated herein by reference.

As used herein the term "toll-like receptor 5" or "TLR5" refers to a toll-like receptor 5 of any species, such as the murine and human polypeptides containing the amino acid sequences set forth as SEQ ID NOs: 6 and 8, of U.S. Published Patent Application No. 20050147627, respectively, encoded by the nucleic acid sequence identified as SEQ ID NOS: 5 and 7, of U.S. Published Patent Application No. 20050147627, respectively. A TLR5 is activated upon binding to flagellin, an immunomodulatory flagellin peptide, or modifications thereof, and other TLR5 agonists. Without being bound by theory, upon activation, a TLR5 induces a cellular response by transducing an intracellular signal that is propagated through a series of signaling molecules from the cell surface to the nucleus. The intracellular domain of TLR5 recruits an adaptor protein, MyD88, which recruits the serine kinase IRAK. IRAK forms a complex with TRAF6, which then interacts with various molecules that participate in transducing the TLR signal. These molecules and other TRL5 signal transduction pathway components stimulate the activity of transcription factors. The activities of signaling molecules that mediate the TLR5 signal, as well as molecules produced as a result of TLR5 activation are TLR5 activities that can be observed or measured. Therefore, a TLR5 activity includes binding to a flagellin polypeptide, immunomodulatory flagellin peptide, or a modification thereof, recruitment of intracellular signaling molecules, as well as downstream events resulting from TLR5 activation, such as the production or activation of Treg cells.

TLR5 also encompasses polypeptides containing minor modifications of a native TLR5, and fragments of a full-length native TLR5, so long as the modified polypeptide or fragment retains one or more biological activities of a native TLR5. A modification of a TLR5 can include additions, deletions, or substitutions of amino acids, so long as a biological activity of a native TLR5 is retained. For example, a modification can serve to alter the stability or activity the polypeptide, or to facilitate its purification. Modifications of polypeptides as described above in reference to flagellin polypeptides and peptides are applicable to TLR5 polypeptides. A "fragment" of a TLR5 is intended to mean a portion of a TLR5 that retains at least about the same activity as a native TLR5, such as binding to a TLR5 agonist.

The term "TLR5 agonist" refers to a compound or agent that selectively activates or increases normal signal transduction through TLR5. The term "TLR5 antagonist" refers to a compound or other agent that selectively inhibits or decreases normal signal transduction through TLR5. A TLR5 agonist or antagonist can alter normal signal transduction through TLR5 indirectly, for example, by modifying or altering the native conformation of TLR5 or a TLR5 ligand. For therapeutic applications, a TLR5 agonist or antagonist has an $EC_{50}$ of less than about $10^{-7}$ M, such as less than $10^{-8}$ M and less than $10^{-9}$ M, although a TRL5 agonist with a higher $EC_{50}$ can be therapeutically useful. Examples of a TLR5 agonist and flagellin and CBLB502. Additional TLR5 agonists are disclosed in U.S. Patent Publication No. 2005/0163764 and U.S. Patent Publication No. 2003/0044429.

Transduced/Transfected: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more nucleic acids encoding a selectable marker and other genetic elements known in the art. Vectors include plasmid vectors, including plasmids for expression in gram negative and gram positive bacterial cells. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

TLR5 Agonists and Flagellin

A TLR5 agonist increases signal transduction through TLR5. TLR5 agonists include small molecules, chemical compounds, antibodies and flagellin. In one example, a TLR5 agonist is an antibody, such as a monoclonal antibody that specifically binds TLR5, or a functional fragment thereof. In other embodiments, a TLR agonist is CBLB502 (see Burdelya et al, Science 2008 Apr. 11; 320 (5873):226-30, incorporated herein by reference). In some embodiments, a TLR5 agonist can have an $EC_{50}$ of less than about $10^{-7}$ M, such as less than $10^{-8}$ M and less than $10^{-9}$ M.

In additional embodiments, a TLR5 agonist is a flagellin polypeptide, or a polynucleotide encoding a flagellin polypeptide. In nature, flagellin is the basic element of bacterial flagella; most gram-negative bacteria have flagella, which are surface structures that provide motility. The flagella are formed from a basal body, a filament, and a hook that connects the basal body to the filament. The filament is formed of a long polymer of a single protein, flagellin, with a small cap protein at the end. Polymerization of flagellin is mediated by conserved regions at the N- and C-termini, whereas the intervening regions of the flagellin protein are very diverse among species. The presence of flagella is strongly related to the infectivity of some pathogenic bacteria. In addition to giving these bacteria the ability to move in the aqueous environment, the flagellum also aids to the attachment of the bacteria to host cells, thereby contributing to the virulence of pathogenic microorganisms. Consistent with its role as TLR5 ligand, flagellin promotes T cell function in vitro and in vivo (McSorley S J et al., Bacterial flagellin is an effective adjuvant for CD4+ T cells in vivo, J Immunol 2002 Oct. 1; 169 (7):3914-9).

Flagellin polypeptides are described, for example, in U.S. Pat. Nos. 6,585,980; 6,130,082; 5,888,810; 5,618,533; and 4,886,748; U.S. Patent Publication No. US 2003/0044429 A1; and Donnelly et al., (2002) J. Biol. Chem. 43: 40456. In nature, flagellin includes (i) a flagellin N-terminal constant region; and (ii) a flagellin C-terminal constant region and (iii) a flagellin hypervariable region between the constant regions. The conserved C-terminal and N-terminal regions of flagellin are well known in the art and have been described, for example, in Mimori-Kiyosue et al., (1997) J. Mol. Virol. 270:222-237; Iino et al., (1977) Ann. Rev. Genet. 11:161-182; and Schoenhals et al, (1993) J. Bacteriol. 175:5395-5402. The size of the constant region will vary somewhat depending on the source of the flagellin protein. In general, the N-terminal constant domain includes the approximately 170 or 180 N-terminal amino acids of the protein, whereas the C-terminal constant domain typically spans the approximately 85 to 100 C-terminal amino acids. The central hypervariable region varies considerably by size and sequence among bacteria, and accounts for most of the difference in molecular mass. The N- and C-terminal constant regions of flagellin polypeptides from a variety of bacteria are known, and others can be readily identified by using known alignment techniques, which are facilitated by the elucidation of the crystal structure of the flagellin monomer (Samatey et al., (2001) Nature 41:331). See also FIG. 1.

A "flagellin N-terminal constant region" and "flagellin C-terminal constant region" as used herein includes active fragments (such as fragments of at least about 50, 100 or 120 amino acids in length) and modifications of any of the foregoing that enhance the immune response (such as, but not limited to, by activating the TLR5 pathway). In one example, the flagellin N-terminal constant regions includes at least 50, at least 100, at least 150, at least 170 or at least 180 amino acids of the N-terminal amino acid sequence of flagellin. In one example, the flagellin C-terminal constant regions includes at least 50, at least 60, at least 70, at least 80, at least 90, or at least 100 amino acids of the C-terminal amino acid sequence of flagellin. In some embodiments, the flagellin N-terminal and/or C-terminal constant region comprises the full-length region or, alternatively, can comprise only a fragment of one or both regions. In particular embodiments, the N-terminal and/or C-terminal constant region comprises a TLR5 recognition site(s) and is able to activate the TLR5 pathway. Regions of the flagellin protein involved in TLR5 signaling have been identified, for example, by Smith et al. (2003) Nat. Immunol. 4:1247-1253 (e.g., amino acids 78-129, 135-173 and 394-444 of *S. typhimurium* flagellin or homologs or modified forms thereof).

An exemplary *E. Coli* flagellin is:

```
                                                              (SEQ ID NO: 1)
MAQVINTNSL  SLITQNNINK  NQSALSSSIE  RLSSGLRINS  AKDDAAGQAI  ANRFTSNIKG

LTQAARNAND  GISVAQTTEG  ALSEINNNLQ  RIRELTVQAT  TGTNSDSDLD  SIQDEIKSRL

DEIDRVSGQT  QFNGVNVLAK  DGSMKIQVGA  NDGETITIDL  KKIDSDTLGL  NGFNVNGKGT

ITNKAATVSD  LTSAGAKLNT  TTGLYDLKTE  NTLLTTDAAF  DKLGNGDKVT  VGGVDYTYNA

KSGDFTTTKS  TAGTGVDAAA  QAADSASKRD  ALAATLHADV  GKSVNGSYTT  KDGTVSFETD

SAGNITIGGS  QAYVDDAGNL  TTNNAGSAAK  ADMKALLKAA  SEGSDGASLT  FNGTEYTIAK

ATPATTTPVA  PLIPGGITYQ  ATVSKDVVLS  ETKAAAATSS  ITFNSGVLSK  TIGFTAGESS

DAAKSYVDDK  GGITNVADYT  VSYSVNKDNG  SVTVAGYASA  TDTNKDYAPA  IGTAVNVNSA

GKITTETTSA  GSATTNPLAA  LDDAISSIDK  FRSSLGAIQN  RLDSAVTNLN  NTTTNLSEAQ

SRIQDADYAT  EVSNMSKAQI  IQQAGNSVLA  KANQVPQQVL  SLLQG
```

An exemplary *S. typhimurium* flagellin is:

```
                                                              (SEQ ID NO: 2)
MAQVINTNSL  SLLTQNNLNK  SQSALGTAIE  RLSSGLRINS  AKDDAAGQAI  ANRFTANIKG

LTQASRNAND  GISIAQTTEG  ALNEINNNLQ  RVRELAVQSA  NSTNSQSDLD  SIQAEITQRL

NEIDRVSGQT  QFNGVKVLAQ  DNTLTIQVGA  NDGETIDIDL  KQINSQTLGL  DSLNVQKAYD

VKDTAVTTKA  YANNGTTLDV  SGLDDAAIKA  ATGGTNGTAS  VTGGAVKFDA  DNNKYFVTIG

GFTGADAAKN  GDYEVNVATD  GTVTLAAGAT  KTTMPAGATT  KTEVQELKDT  PAVVSADAKN

ALIAGGVDAT  DANGAELVKM  SYTDKNGKTI  EGGYALKAGD  KYYAADYDEA  TGAIKAKTTS

YTAADGTTKT  AANQLGGVDG  KTEVVTIDGK  TYNASKAAGH  DFKAQPELAE  AAAKTTENPL

QKIDAALAQV  DALRSDLGAV  QNRFNSAITN  LGNTVNNLSE  ARSRIEDSDY  ATEVSNMSRA

QILQQAGTSV  LAQANQVPQN  VLSLLR
```

Amino acid sequences at least about 90%, at least about 95%, at least about 97%, at least about 98% or at least about 99% identical to SEQ ID NO: 1 or SEQ ID NO: 2 can be used in the methods disclosed herein. To determine the percent identity of two amino acid sequences, the sequences are aligned for optimal comparison purposes. The percent identity between the two sequences is a function of the number of identical positions shared by the sequences (percent identity=number of identical positions/total number of positions×100). In one embodiment, the two sequences are the same length. The percent identity between two sequences can be determined using techniques similar to those described below, with or without allowing gaps. In calculating percent identity, typically exact matches are counted.

Methods of alignment of sequences for comparison are well known in the art. Various programs and alignment algorithms are described in: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237; Higgins and Sharp (1989) *CABIOS* 5:151; Corpet et al. (1988) *Nucleic Acids Research* 16:10881; and Pearson and Lipman (1988) *Proc. Natl. Acad. Sci. U.S.A.* 85:2444. Altschul et al. (1994) *Nature Genet.* 6:119 presents a detailed consideration of sequence alignment methods and homology calculations.

The NCBI Basic Local Alignment Search Tool (BLAST) (Altschul et al. (1990) *J. Mol. Biol.* 215:403) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet. Alternatively, alterations may be made to the protein sequence of many proteins at the amino or carboxy terminus without substantially affecting activity.

In some embodiments, the flagellin polypeptide includes (or consists of) the N-terminal constant regions. The N-terminal constant region includes the N-terminal RINSA (SEQ ID NO: 3) domain (amino acids 31-52 of the *S. dublin* flagellin) as described by Eaves-Pyles et al. (2001) J. Immunology 167: 7009-7016. In other embodiments, the N-terminal constant region comprises the D1 and D2 domains, and the C-terminal constant region comprises the D1 and D2 domains (Eaves-Pyles et al. (2001) J. Immunology 167: 7009-7016). In other embodiments, the flagellin N-terminal and/or C-terminal constant region comprises, consists of, or consists essentially of the peptide GAVQNRFNSAIT (SEQ ID NO:4) as described by U.S. Patent Publication No. US 2003/0044429 A1 or a homolog or modification thereof.

In additional embodiments, the N-terminal constant domain comprises (or consists of) the "motif N" (e.g., amino acids 98-108 of the *S. muenchen* flagellin) and/or the C-terminal constant domain comprises the "motif C" (e.g., amino acids 441-449 of the *S. muenchen* flagellin) identified by Kanneganti et al., (2004) J. Biol. Chem. 279:5667-5676). In other illustrative embodiments, the N-terminal constant domain comprises amino acids 88 to 97 of the *P. aeruginosa* flagellin (see, e.g., Verma et al., (2005) Infect. Immun. 73:8237-8246) or a homolog or modified form thereof that enhances an immune response to the tumor antigen.

The wild-type amino acid sequence of a flagellin polypeptide, such as the full length polypeptide or the N-terminal and/or C-terminal regions can be modified, such as by using conservative amino acid substitutions to increase an immune response to an opportunistic infection and/or decrease GVHD. In some examples, the flagellin polypeptide includes at most 2, at most 5, at most 10, at most 15 or at most 20 conservative amino acid substitutions as compared to the wild-type amino acid sequence. The flagellin polypeptide, including the N-terminal constant, C-terminal constant and hypervariable regions can be derived from flagellins from any suitable source, with some or all of these regions being derived from the same organism or from different organisms. A number of flagellin genes have been cloned and sequenced (see, e.g., Kuwajima et al., (1986) J. Bact. 168:1479; Wei et al., (1985) J. Mol. Biol. 186:791-803; and Gill et al., (1983) J. Biol. Chem. 258:7395-7401). Non-limiting sources of flagellins include but are not limited to *S. enteritidis, S. typhimurium, S. dublin, H. pylori, V. cholera, S. marcesens, S. flexneri, S. enterica, T. pallidum, L. pneumophilia, B. burgdorferi, C. difficile, A. tumefaciens, R. meliloti, B. clarridgeiae, R. lupine, P. mirabilis, B. subtilis, P. aeruginosa,* and *E. coli.* These amino acid sequences are publicly available in GENBANK®, as of Oct. 3, 2008, see for example Accession Nos. BAB59884, CAA02137, YP001217666, CAL35450, AAN74969, and BAC44986, as of Oct. 2, 2009, which are incorporated by reference herein.

Thus, chimeric molecules, such as a flagellin that includes the C-terminal region of an *E. coli* flagellin and the N. terminal region of an *S. typhimurium* flagellin are of use in the methods disclosed herein. Fusion polypeptides including an antigen of a pathogen, such as an opportunistic infection (see below), and a flagellin polypeptide can also be produced.

The methods disclosed herein can also use nucleic acids encoding a flagellin polypeptide, or a fragment thereof, such as a polypeptide that includes the N-terminal domain, the C-terminal domain, or both. Nucleic acids encoding a flagellin polypeptide at least about 90%, 95%, 98% or 99% identical to SEQ ID NO: 1 or SEQ ID NO: 2, or any flagellin amino acid sequence can also be utilized in the methods disclosed herein. Computer programs for determining sequence identity are disclosed above. Variants of the flagellin-encoding nucleotide sequences include those sequences that encode a flagellin polypeptide disclosed herein but that differs conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the flagellin polypeptides disclosed herein. Variants also include a nucleic acid molecule that hybridizes to a nucleic acid molecule encoding a flagellin polypeptide, or a complement thereof, under stringent conditions.

One of skill in the art can readily introduce changes by mutation into the flagellin nucleotide sequences, thereby leading to changes in the amino acid sequence of the encoded flagellin polypeptides, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis, including PCR amplifications that alter or extend the protein coding sequence by virtue of inclusion of amino acid encoding sequences in the oligonucleotides utilized in the PCR amplification. Such variant nucleotide sequences may also be used in the methods provided herein. Hybridization of such sequences may be carried out under stringent conditions. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (for example, 10 to 50 nucleotides) and at least about 60° C. for long probes (for example, greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may have about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the Tm can be approximated from the equation of Meinkoth and Wahl (1984) *Anal. Biochem.* 138:267-284: Tm=81.5° C.+16.6(log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.).

Expression vectors can be used to deliver nucleotides that encode a flagellin polypeptide. Expression systems and expression vectors are known in the art. In general, an expression vector will include in the 5'-3' direction of transcription, a transcriptional and translational initiation region (a promoter), a DNA sequence encoding a protein of interest, and a transcriptional and translational termination region (termination region). The expression vector may be any expression vector that is capable of directing expression of a gene in a host cell, including prokaryotic, eukaryotic, or viral vector. These include, for example, microorganisms such as bacteria transformed with recombinant bacteriophage, plasmid, or cosmid DNA expression vectors; yeast transformed with yeast expression vectors; insect cell systems infected with virus expression vectors (for example, baculovirus), insects infected with virus expression vectors (for example, fall army worm infected with baculovirus); plant cell systems transformed with virus expression vectors (for example, cauliflower mosaic virus, CaMV; tobacco mosaic virus; TMV) or with bacterial expression vectors (for example, Ti or bacterial plasmids); or animal cell systems.

Examples of such vectors include pCMV-Script cytomeglovirus expression vectors for expression in mammalian cells, pESP and pESC vectors for expression in *S. pombe* and *S. cerevesiae*, pET vectors for expression in bacteria, pSPUTK vectors for high-level transient expression, and pPbac and pMbac vectors for expression in fall army worm (SF9) cells. Such vectors are available commercially from suppliers such as, for example, Invitrogen (Carlsbad, Calif.) or Stratagene (La Jolla, Calif.). In the use of viral vectors, it is understood that defective viral vectors (vectors that are genetically engineered to deliver a gene or gene product to a host but which cannot replicate in a host) are preferred. Procedures for the practice of in vitro and in vivo expression are well known to those of skill in the art and are further available with the specific expression products and cell lines from commercial suppliers.

Host cells may be transformed with a vector containing a nucleic acid molecule with a sequence that encodes, for example, a flagellin polypeptide. The host cell may be any eukaryotic or prokaryotic cell such as, for example a human, murine, *rattus*, bovine, insect, yeast or bacteria. Specific cell lines are well known to those of skill in the art and are available from suppliers such as the American Tissue Type Collection (ATCC, Manassas, Va.) and Stratagene (La Jolla, Calif.) and the like.

The control elements or regulatory sequences necessary for the proper expression of the insert may include promoters or enhancers (including both proximal and distal control elements) that interact with the host proteins to carry out transcription and translation. Such elements may vary in their strength and specificity and are known to those in the art. Depending on the vectors system and host utilized, any number of suitable transcription and translation elements, including constitutive and inducible promoters, may be used. For example, the LacZ promoter may be used in a bacterial cell; the baculovirus polyhedrin promoter may be used in an insect cell; plant promoters such as heat shock promoters, and storage protein promoters, plant virus promoters and the like may be used in a plant cell. In a mammalian cell expression system, an SV40 promoter or EBV promoter may be used, for example.

Methods and protocols for both prokaryotic and eukaryotic expression systems are generally known to those in the art. Further, the cells, vectors, and growth medium may be purchased from commercial suppliers. The catalogs and product literature of commercial suppliers provide detailed protocols to enable the expression of proteins in prokaryotic and eukaryotic systems including bacterial, yeast, insect, insect cell, and mammalian cell systems.

Methods that are known to those skilled in the art may be used to construct expression vectors containing sequences encoding, for example, flagellin and appropriate transcriptional and translational control elements. These methods include in vitro recombinant DNA techniques, synthetic techniques, and in vivo genetic recombination.

Methods of Treatment and Pharmaceutical Compositions

Methods are provided herein for treating or preventing graft-versus host disease (GVHD). The methods include administering to a subject a therapeutically effective amount of TLR5 agonist, such as but not limited to a flagellin polypeptide or a polynucleotide encoding the polypeptide, thereby treating or preventing GVHD. The subject can be any subject in need of treatment for GVHD. A subject in need of treatment for GVHD includes a subject who is at risk for GVHD, such as a subject who has received, or who is about to receive, a bone marrow transplant or a hematopoietic stem cell transplant. Thus, in some embodiments, the disclosed methods are methods for preventing GVHD in a subject. The subject can be any subject, including human and veterinary subjects.

When T cells are transplanted from a donor into a recipient, the recipient's immune system can be depleted or ablated by any method known in the art. Examples of immunodepleting methods include, but are not limited to, the use of chemotherapy, radiotherapy and anti-lymphocyte antibodies such as Campath, ATG, ALG, OKT3 (anti-CD3) and anti-CD4 and anti-CD8 antibodies. Such treatment is termed a conditioning regimen and is used to prepare the recipient to take (and not reject) the transplant of lymphocytes and marrow stem cells and to debulk the malignant disease if the recipient is being treated for a malignant disease.

In one example, the recipient's immune system is depleted or ablated by the administration of total body irradiation and cyclophosphamide. In another example, fludarabine and other chemotherapy such as busulfan cyclophosphamide or melfalan is administered to deplete T cells and to debulk the malignant disease. A therapeutically effective amount of bone marrow or hematopoietic stem cells is then administered to the subject, using method well known to those of skill in the art.

Thus, the subject can have received a bone marrow or hematopoietic stem cell transplant, or can have a disorder that will be treated by a bone marrow or hematopoietic stem cell transplant. In some embodiments, these subjects can include subjects diagnosed with one or more disorders. In some embodiments, the subject has a malignancy, such as a hematologic malignancy, such as a leukemias, for example, acute lymphoblastic leukemia (ALL), acute myelogenous leukemia (AML), chronic lymphocytic leukemia (CLL), chronic myelogenous leukemia (CML), accelerated phase or blast crisis, lymphomas, Hodgkin's disease, non-Hodgkin's lymphoma, or such as a myelomas, for example multiple myeloma (Kahler's disease). In other embodiments, the subject has a solid tumor, such as a neuroblastoma, demoplastic small round cell tumor, Ewing's sarcoma, or choriocarcinoma. In other embodiments, the subject has a hematologic disorder, such myelodysplasia, paroxysmal nocturnal hemoglobinuria (PNH; severe aplasia), aplastic anemia, or a myeloproliferative disorder (for example, Polycythemia vera or Essential thrombocytosis) In further embodiments, the subject has a metabolic disorder, such as amyloid light chain (AL) amyloidosis. The subject can also have an environmentally-induced disease, such as radiation poisoning.

Furthermore, the subject can have a congenital disorder, such as a lysosomal storage disorder, for example a lipidoses (disorders of lipid storage), which include neuronal ceroid lipofuscinoses, infantile neuronal ceroid lipofuscinosis (INCL, Santavuori disease), Jansky-Bielschowsky disease (late infantile neuronal ceroid lipofuscinosis); sphingolipidoses, such as Niemann-Pick disease or Gaucher disease; leukodystrophies, such ss adrenoleukodystrophy, metachromatic leukodystrophy, or Krabbe disease (globoid cell leukodystrophy); mucopolysaccharidoses, such as Hurler syndrome (MPS I H, α-L-iduronidase deficiency), Scheie syndrome (MPS I S), Hurler-Scheie syndrome (MPS I H-S), Hunter syndrome (MPS II, iduronidase sulfate deficiency), Sanfilippo syndrome (MPS III), Morquio syndrome (MPS IV), Maroteaux-Lamy syndrome (MPS VI), Sly syndrome (MPS VII); a glycoproteinoses, such as Mucolipidosis II (I-cell disease), fucosidosis, aspartylglucosaminuria, or alpha-mannosidosis. The subject can also have an immunodeficiency, such as a T cell deficiency, a B cell deficiency, a phagocyte disorder. Exemplary immunodeficiencies include ataxia telangiectasia, DiGeorge syndrome, Severe combined immunodeficiency (SCID), Wiskott-Aldrich syndrome, Kostmann syndrome, Shwachman-Diamond syndrome, Griscelli syndrome, type II, or NF-Kappa-B Essential Modulator (NEMO) deficiency (Inhibitor of Kappa Light Polypeptide Gene Enhancer in B Cells Gamma Kinase deficiency). The subject can also have a hematologic diseases, sickle cell disease, β thalassemia major (Cooley's anemia), aplastic anemia, Diamond-Blackfan anemia, Fanconi anemia, cytopenia, such as amegakaryocytic thrombocytopenia, or hemophagocytic lymphohistiocytosis (HLH).

GVHD can be a complication of bone marrow transplantation, such as allogeneic bone marrow transplantation, or hematopoietic stem cell transplantation. Cells from the transplanted bone marrow or stem cells recognize the host tissue is foreign and produce an immune response against host tissue. Briefly, T cells from the bone marrow graft produce cytokines, such as Tumor Necrosis Factor-alpha (TNF-α) and interferon-gamma (IFNγ). A wide range of host antigens can initiate GVHD, such as the human leukocyte antigens (HLAs). However, GVHD has been documented to occur even when HLA-matched siblings are the donor and recipients, due to differences in the minor histocompatability antigens. GVHD occurs in two forms, an acute form that occurs within about 100 days of bone marrow/hematopoietic stem cell transplant and a chronic form that occurs after more than about 100 days of bone marrow/hematopoietic stem cell transplant. Acute GVHD is characterized by selective damage to the liver, skin, mucosa and the gastrointestinal tract. Other target organs of GVHD include the organs of the immune system, such as the thymus, and the lungs (in the form of idiopathic pneumonitis). Methods are disclosed herein for treating either acute or chronic GVHD.

Acute GVHD of the gastrointestinal tract can result in watery diarrhea, abdominal pain, nausea, and vomiting. This is typically diagnosed via intestinal biopsy. Liver GVHD is measured by the bilirubin level in acute patients. Skin GVHD results in a diffuse maculopapular rash, sometimes in a lacy pattern. Acute GVHD can be staged as an overall grade (skin-liver-gut, with each organ staged individually from a low grade of I to a high grade of IV. Patients with grade IV GVHD usually have a poor prognosis. Chronic GVHD damages the same organs as the acute form of the disease, but also causes changes to the connective tissue, the skin and the exocrine glands. The methods disclosed herein can be used to treat a subject with chronic or acute GVHD. The subject can have any grade of GVHD. In some embodiments, the methods result in a decrease in a sign or symptom of GVHD, such as but not limited to, a decrease in the bilirubin level, a decrease in the extent of the maculopapular rash, or a reduction in the volume of diarrhea. The number of T-cells in the blood can rise when GVHD is effectively treated.

Generally, the methods disclosed herein include the administration of a therapeutically effective amount of a TRL5 agonist, such as flagellin polypeptide, or a nucleic acid encoding a flagellin polypeptide, to a subject with, or at risk for, GVHD. The TLR5 agonist, such as a flagellin polypeptide, or the nucleic acid encoding the flagellin polypeptide, can be administered prior to, concurrently with, or subsequent to, bone marrow or hematopoietic stem cell transplantation. In addition, the TLR5 agonist, such as the flagellin polypeptide, or the nucleic acid encoding the flagellin polypeptide, can be administered more than once, such as in daily, weekly, bi-monthly or monthly intervals over a period of time, such as about one week, about two weeks, about three weeks, about one month, about two months, about three months, about four months, about five months, about six months, about a year, or longer.

It is known that bone marrow recipients and hematopoietic stem cell recipients can develop severe opportunistic infections and may die of infection. Methods are disclosed herein for the treatment and/or prevention of an opportunistic infection in a subject. The opportunistic infection can be a viral, fungal or bacterial infection. These methods include administration of a flagellin polypeptide, as disclosed herein, or a polynucleotide encoding the flagellin polypeptide.

The methods can include administering to the subject an antigen from the opportunistic infection. In several embodiments, the opportunistic infection is cytomegalovirus, *Cryptococcus neoformans, Entamoeba histolytica, Toxoplasma brucei, Candida albicans*. The method can also include administering to the subject an antigen from Human Immunodeficiency Virus, *Staphlococcus aureus, Steptococcus pyogenes, Pseudomas aeruginosa, Acinteobacter baumanni, Toxoplasma gondii, Pneumocystitis carinii*, or *Aspergillus*. Examples of microorganisms that may cause infections in transplant patients (as well as non-transplant patients) include those from, without limitation, *Salmonella enteriditis, Listeria monocytogenes, M. leprae, Staphylococcus aureus, Escherichia coli, Streptococcus pneumoniae, Borrelia burgdorferi, Actinobacillus pleuropneumoniae, Helicobacter pylori, Neisseria meningitidis, Yersinia enterocolitica, Bordetella pertussis, Porphyromonas gigivalis*, mycoplasma, *Histoplasma capsulatum, Cryptococcus neoformans, Chlamydia trachomatis, Candida albicans, Plasmodium falciparum, Entamoeba histolytica, Toxoplasma brucei, Toxoplasma gondii, Leishmania major*, human immunodeficiency virus 1 and 2, influenza virus, measles virus, rabies virus, hepatitis virus A, B, and C, rotaviruses, papilloma virus, respiratory syncytial virus, feline immunodeficiency virus, feline leukemia virus, and simian immunodeficiency virus. The antigen can be from a mycoplasmal species including *Mycoplasma hyopneumoniae* (swine); *M. hyorhinis* (swine); *M. hyosynoviae* (swine); *M. gallisepticum* (avian); *M. synoviae* (avian); *M. meleagridis* (avian); *M. gallinarum* (avian); *M. bovis* (bovine/caprine); *M. bovoculi* (bovine); *M. dispar* (bovine); *M. capricolumn* (caprine/bovine); *M. mycoides* subspecies *mycoides* (Large Colony (LC) and small colony (SC)) (ovine/caprine); *M. mycoides* subspecies *capri* (ovine/caprine); *M. agalactiae* (caprine/ovine); *M. pneumoniae* (human); *M. genitalium* (human); *M. penetrans* (human); *M. fermentans* (human); *M. hominis* (human); and all *Ureaplasma urealyticum* serotypes (human). Compositions can be produced including a flagellin polypeptide, or a polynucleotide encoding the flagellin polypeptide, and an antigen from a pathogen, such as an opportunistic infection, or a nucleic acid encoding the antigen.

The methods can include administering a vaccine to the subject, such as a subunit vaccine, a heat-killed vaccine or an attenuated vaccine. In some examples the vaccine is a vaccine for diphtheria, a vaccine for tetanus, Prevnar, 23 valent pneumococcal vaccine, measles mumps and rubella (MMR), polio vaccine, Hepatitis B vaccine, or *Hemophilus influenza* vaccine. The TRL5 agonist, such as the flagellin polypeptide, or the polynucleotide encoding the flagellin polypeptide, can be administered prior to, concurrently with, or subsequent to the administration of an antigen from an opportunistic infection or a vaccine. In some embodiments, the antigen is delivered as part of a vaccine.

A number of vaccines against infectious diseases are currently approved for use in the United States, examples of which are listed below in Table 3.

TABLE 3

Approved Vaccines for Immunization and Distribution in the U.S.

| Product Name | Trade Name |
|---|---|
| Anthrax Vaccine Adsorbed | BIOTHRAX |
| BCG Vaccine | TICE BCG |
| BCG Vaccine | MYCOBAX |
| Diphtheria & Tetanus Toxoids Adsorbed | None |
| Diphtheria & Tetanus Toxoids Adsorbed | None |
| Diphtheria & Tetanus Toxoids & Acellular Pertussis Vaccine Adsorbed | TRIPEDIA |
| Diphtheria & Tetanus Toxoids & Acellular Pertussis Vaccine Adsorbed | INFANRIX |
| Diphtheria & Tetanus Toxoids & Acellular Pertussis Vaccine Adsorbed | DAPTACEL |
| Diphtheria & Tetanus Toxoids & Acellular Pertussis Vaccine Adsorbed, Hepatitis B (recombinant) and Inactivated Poliovirus Vaccine Combined | PEDIARIX |
| Diphtheria and Tetanus Toxoids and Acellular Pertussis Adsorbed and Inactivated Poliovirus Vaccine | KINRIX |
| Diphtheria and Tetanus Toxoids and Acellular Pertussis Adsorbed, Inactivated Poliovirus and Haemophilus b Conjugate (Tetanus Toxoid Conjugate) Vaccine | PENTACEL |
| Haemophilus b Conjugate Vaccine (Diphtheria CRM197 Protein Conjugate) | HIBTITER |
| Haemophilus b Conjugate Vaccine (Meningococcal Protein Conjugate) | PEDVAXHIB |
| Haemophilus b Conjugate Vaccine (Tetanus Toxoid Conjugate) | ACTHIB |
| Haemophilus b Conjugate Vaccine (Meningococcal Protein Conjugate) & Hepatitis B Vaccine (Recombinant) | COMVAX |
| Hepatitis A Vaccine, Inactivated | HAVRIX |
| Hepatitis A Vaccine, Inactivated | VAQTA |
| Hepatitis A Inactivated and Hepatitis B (Recombinant) Vaccinee | TWINRIX |

TABLE 3-continued

Approved Vaccines for Immunization and Distribution in the U.S.

| Product Name | Trade Name |
| --- | --- |
| Hepatitis B Vaccine (Recombinant) | RECOMBIVAX HB |
| Hepatitis B Vaccine (Recombinant) | ENGERIX-B |
| Human Papillomavirus (Types 6, 11, 16, 18) Recombinant Vaccine | GARDASIL |
| Influenza Virus Vaccine | AFLURIA |
| Influenza Virus Vaccine, H5N1 | None |
| Influenza Virus Vaccine, Trivalent, Types A and B | FLULAVAL |
| Influenza Virus Vaccine, Live, Intranasal | FLUMIST |
| Influenza Virus Vaccine, Trivalent, Types A and B | FLUARIX |
| Influenza Virus Vaccine, Trivalent, Types A and B | FLUVIRIN |
| Influenza Virus Vaccine, Trivalent, Types A and B | FLUZONE |
| Japanese Encephalitis Virus Vaccine Inactivated | JE-VAX |
| Measles Virus Vaccine, Live | ATTENUVAX |
| Measles and Mumps Virus Vaccine, Live | M-M-Vax |
| Measles, Mumps, and Rubella Virus Vaccine, Live | M-M-R II |
| Measles, Mumps, Rubella and Varicella Virus Vaccine, Live | PROQUAD |
| Meningococcal Polysaccharide (Serogroups A, C, Y and W-135) Diphtheria Toxoid Conjugate Vaccine | MENACTRA |
| Meningococcal Polysaccharide Vaccine, Groups A, C, Y and W-135 Combined | MENOMUNE-A/C/Y/W-135 |
| Mumps Virus Vaccine Live | MUMPSVAX |
| Plague Vaccine | None |
| Pneumococcal Vaccine, Polyvalent | PNEUMOVAX 23 |
| Pneumococcal 7-valent Conjugate Vaccine (Diphtheria CRM197 Protein) | PREVNAR |
| Poliovirus Vaccine Inactivated (Human Diploid Cell) | POLIOVAX |
| Poliovirus Vaccine Inactivated (Monkey Kidney Cell) | IPOL |
| Rabies Vaccine | IMOVAX |
| Rabies Vaccine | RABAVERT |
| Rabies Vaccine Adsorbed | No Trade Name |
| Rotavirus Vaccine, Live, Oral | ROTARIX |
| Rotavirus Vaccine, Live, Oral, Pentavalent | ROTATEQ |
| Rubella Virus Vaccine Live | MERUVAX II |
| Smallpox (Vaccinia) Vaccine, Live | ACAM2000 |
| Smallpox Vaccine, Dried, Calf Lymph Type | DRYVAX |
| Tetanus & Diphtheria Toxoids Adsorbed for Adult Use | None |
| Tetanus & Diphtheria Toxoids Adsorbed for Adult Use | DECAVAC |
| Tetanus & Diphtheria Toxoids Adsorbed for Adult Use | TENIVAC |
| Tetanus Toxoid | None |
| Tetanus Toxoid Adsorbed | None |
| Tetanus Toxoid Adsorbed | None |
| Tetanus Toxoid, Reduced Diphtheria Toxoid and Acellular Pertussis Vaccine, Adsorbed | ADACEL |
| Tetanus Toxoid, Reduced Diphtheria Toxoid and Acellular Pertussis Vaccine, Adsorbed | BOOSTRIX |
| Typhoid Vaccine Live Oral Ty21a | VIVOTIF |
| Typhoid Vi Polysaccharide Vaccine | TYPHIM VI |
| Varicella Virus Vaccine Live | VARIVAX |
| Yellow Fever Vaccine | YF-VAX |
| Zoster Vaccine, Live | ZOSTAVAX |

In some embodiments, the methods include administering an antigen of interest from the opportunistic infection. The antigen of interest can be produced by any of a wide variety of infectious microorganisms that are opportunistic infections such as bacteria, fungi, yeast, mycoplasma, or viruses.

The TLR5 agonist, such as the flagellin polypeptide or the polynucleotide encoding the flagellin polypeptide can be administered by any means known to one of skill in the art (see Banga, "Parenteral Controlled Delivery of Therapeutic Peptides and Proteins," in *Therapeutic Peptides and Proteins*, Technomic Publishing Co., Inc., Lancaster, Pa., 1995). Flagellin or a nucleic acid encoding the flagellin polypeptide can be administered with another TLR5 agonist and/or another immunosuppressive agent. It can be administered in conjunction with a vaccine or an antigen of an opportunistic infection. The method can include measuring a T cell or a B cell response to the opportunistic infection.

Suitable routes of administration include intramuscular, intraperitoneal, subcutaneous, or intravenous injection, but even oral, nasal, transdermal, inhalation or anal administration is contemplated. In one embodiment, administration is by subcutaneous or intramuscular injection. To extend the time during which flagellin is available, it can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release.

Thus, examples of compositions include liquid preparations for orifice (e.g., oral, nasal, anal, vaginal, peroral, intragastric) administration such as suspensions, syrups or elixirs; and preparations for parenteral, subcutaneous, intradermal, intramuscular or intravenous administration (e.g., injectable administration, including the use of needleless injectors) such as sterile suspensions or emulsions, are provided. In such compositions the antigen(s) may be in admixture with a suitable carrier, diluent, or excipient such as sterile water, physiological saline, glucose or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard texts, such as *Remington's Pharmaceutical Science*, 17th edition, 1985, incorporated herein by reference, may be consulted to prepare suitable preparations, without undue experimentation. The compositions can also be lyophilized.

Suitable dosages can also be determined by one of skill in the art. For example, typical dosages of a flagellin polypeptide can be from about 5 µg/ml to about 150 µg/ml, and other dosages can be from about 15 to about 150 µg/dose. Single or multiple administrations of the compositions are administered depending on the dosage and frequency as required and tolerated by the subject. In one embodiment, the dosage is administered once as a bolus, but in another embodiment can be applied periodically until either a therapeutic result is achieved. Generally, the dose is sufficient to treat or ameliorate symptoms or signs of disease such as GVHD without producing unacceptable toxicity to the subject.

In another embodiment, a nucleic acid encoding a flagellin polypeptide is utilized (e.g., see Robinsion et al., *Nat. Med.*, 5 (5):526-34, 1999). Thus, a method is provided for treating GVHD, or an opportunistic infection, such as a viral, fungal or bacterial infection, by providing a therapeutically effective amount of a nucleic acid encoding the flagellin polypeptide. Delivery of the polynucleotide encoding the flagellin can be achieved using a recombinant expression vector such as a chimeric virus or a colloidal dispersion system, or through the use of targeted liposomes. For example, about 10 µg to about 1 mg of DNA can be utilized, such as about 10-100 µg, or about 50 µg, of a DNA construct can be injected intradermally three times at two week intervals to produce the desired therapeutic effect Various viral vectors which can be utilized for administration of nucleic acids include, but are not limited to, adenoviral, herpes viral, or retroviral vectors. In one embodiment, a retroviral vector such as a derivative of a murine or avian retroviral vector is utilized. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). In addition, when the subject is a human, a vector such as the gibbon ape leukemia virus (GaLV) is utilized. A number of additional retroviral vectors can incorporate multiple genes. The vectors can transfer or incorporate a gene for a selectable marker so that transduced cells can be identified and generated. By inserting a nucleic acid encoding a flagellin polypeptide into the viral vector, along with another gene which encodes the ligand for a receptor on a specific target cell, for example, the vector is rendered target specific. Retroviral vectors can be made target specific by attaching, for example, a sugar, a glycolipid, or a protein. Targeting can also be accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines which have deletions of the packaging signal include, but are not limited to, Q2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for therapeutic polynucleotides encoding a polypeptide, such as a flagellin polypeptide is a colloidal dispersion system. Colloidal dispersion systems include macromolecule complexes, nano-capsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 μm, can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.* 6:77, 1981). In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques* 6:682, 1988; see also U.S. Pat. No. 6,270,795).

The composition of the liposome is usually a combination of phospholipids, particularly high-phase-transition-temperature phospholipids, usually in combination with steroids, such as cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Intensive prophylaxis with immunosuppressive drugs has been used for all subjects undergoing allogeneic bone marrow transplantation. The immunosuppressive drugs can be used in combination with the methods disclosed herein. Compounds in use include cyclosporine, tacrolimus, methotrexate, mycophenolate mofetil, corticosteroids or antithymocyte globulin (ATG). The decrease in the incidence and severity of acute GVHD is in large part due to the widespread prophylactic use of these drugs, particularly cyclosporine or tacrolimuns in combination with methotrexate. Additionally, monoclonal antibodies (for example, anti-CD3, anti-CD5, and anti-IL-2 antibodies), Mycophenolate mofetil, Alemtuzumab, Antithymocyte globulin (ATG), and Sirolimus are of use to treat acute GVHD. Tacrolimus, Mycophenolate mofetil, Antithymocyte globulin (ATG), Thalidomide, Daclizumab, Extracorporeal photopheresis, Infliximab, and Clofazimine are of use to treat chronic GVHD. The present methods can be combined with the use of a therapeutically effective amount of one or more of these compounds.

The present methods can also include administering a therapeutically effective amount of another TLR5 agonist to the subject, such as an antibody agonist.

The disclosure is illustrated by the following non-limiting Examples.

EXAMPLES

In spite of extensive research to control Graft-vs-host disease (GVHD) in allogeneic hematopoietic stem cell transplantation (HSCT), it still remains a major clinical problem that contributes to the 25-50% early mortality associated with this procedure. GVHD is the result of recognition of host allo-antigen by donor T cells. A number of immunosuppressive drugs such as cyclosporine, corticosteroids, and methotrexate are usually used to control GVHD as pharmacological prophylaxis, but the desired prophylactic immunosuppression effects are often incomplete, and patients experience significant drug-related toxicities and increased infections due to systemic immunosuppression. Therefore, alternative approaches to control GVHD without causing systemic immuno-suppression are highly desirable.'

Flagellin (see FIG. 1), a bacterial protein and a TLR5 agonist was tested to determine its effectiveness in treating GVHD in allogeneic BMT and the subsequent ability to protect HSCT host from viral infection.

Example 1

Materials and Methods

Figure 2:
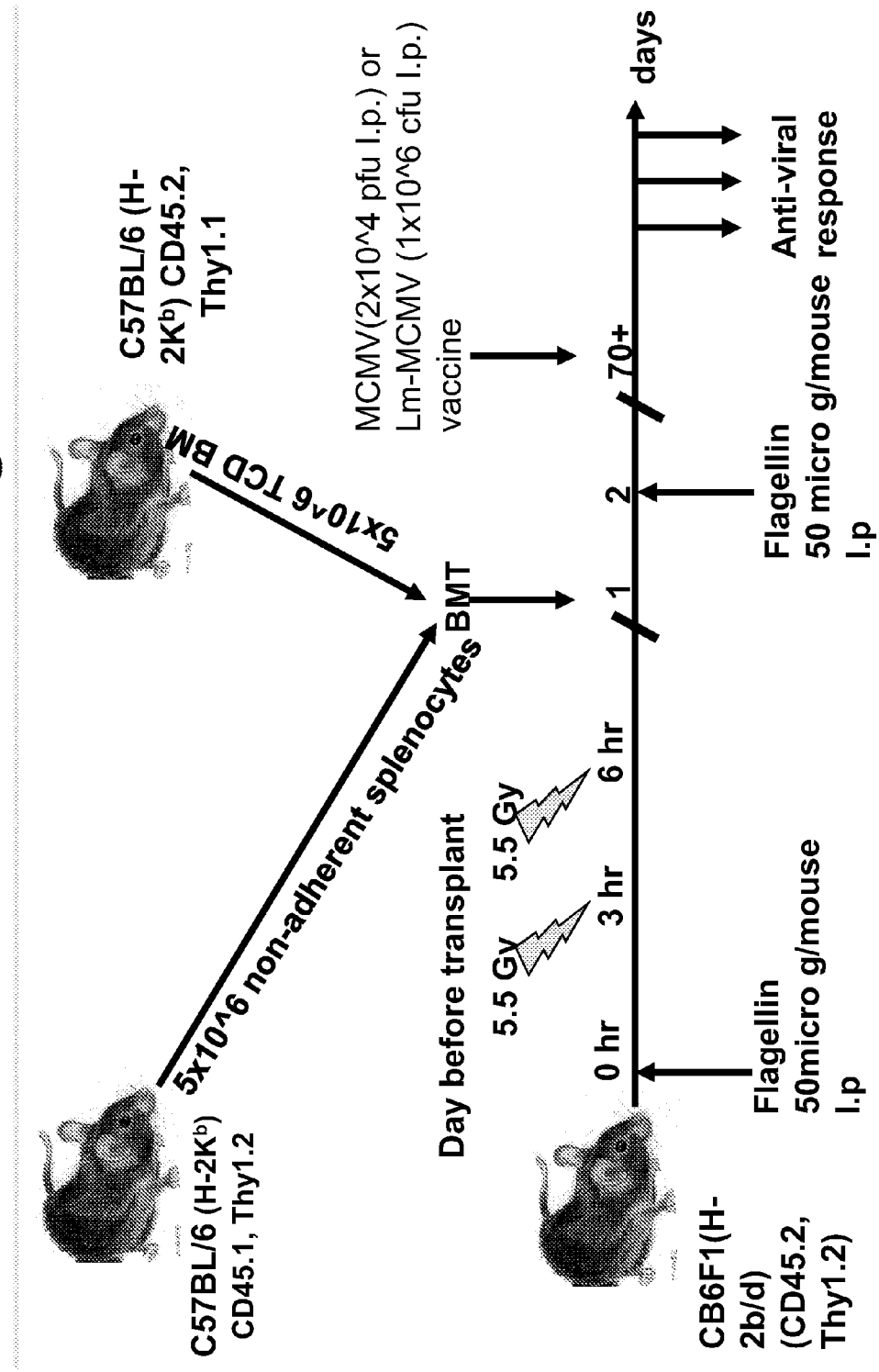
FIG. 2 is a schematic diagram of an experimental model to demonstrate that flagellin reduces GVHD, improves survival, and increases the anti-viral response to cytomegalovirus in animals receiving a bone marrow transplant. CB6F1 mice were injected intraperitoneally (i.p.) with 50 micrograms of flagellin, and then were irradiated (5.5 Gy) 3 and 6 hours later for myeloablation (5.5 Gy each dose). 24 hours after the flagellin injection, mice were transplanted by intravenous (i.v.) infusion of 5×10$^6$ bone marrow cells (T-cell depleted) and 5×10$^6$ plastic non-adherent splenocytes. The transplanted cells were isolated from C57BL/6 donors that differs from one another (as well as from the hematopoietic stem cell transplant (HSCT) recipient) by congenic markers (CD45 and Thy1). The HSCT recipients received a second i.p. injection of flagellin (50 micro g/mouse) 24 hours after HSCT. Mice were longitudinally tracked to monitor weight loss (as a marker for GVHD) and survival. At approximately 80 days after HSCT, some surviving mice from each group were infected with murine cytomegalovirus (MCMV) or a *Listeria*-MCMV vaccine to track the resulting anti-MCMV immune response.

Irradiated (11 Gy) CB6F1 (C57BL6×BALB/c) (H-2b/d, CD45.2+, Thy1.2+) recipient mice were transplanted with $5\times10^6$ T cell depleted (TCD) bone marrow cells and $5\times10^6$ or $10\times10^6$ plastic non-adherent splenocytes from naive C57BL/6 congenic donors (H-2b, CD45.2+, Thy1.1+) and (H-2b, CD45.1+, Thy1.2+) respectively. Fifty micrograms (μg) flagellin per recipient mouse was administered intraperitoneally (i.p.) before irradiation and 24 hours after HSCT. Transplant recipients that received no flagellin were used as controls. Acute and chronic GVHD was monitored twice weekly by measuring weight loss and clinical signs of hair loss, ruffled fur, diarrhea, and decreased activity. Moribund mice and animals with >25% weight loss were euthanized and considered to have died on the day following euthanasia for analysis of post-transplant survival. After 100+ days post-transplant, recipient mice were infected with $5\times10^3$ murine cytomegalovirus (MCMV) pfu i.p. Blood immunological profiles were determined by bleeding mice on day 10-post infection. After day 35 post infection, recipients were sacrificed and lymphocytes were harvested from the PBMC, spleen, liver and thymus. Flow cytometry was used to quantitate T cell chimerism and CD62L+ T cells, anti-viral CD8+ T cells and CD4+CD25+ foxp3+ regulatory T cells. A schematic diagram of an exemplary protocol is shown in FIG. 2.

Example 2

Effect of Flagellin Treatment on Survival

Figure 3:
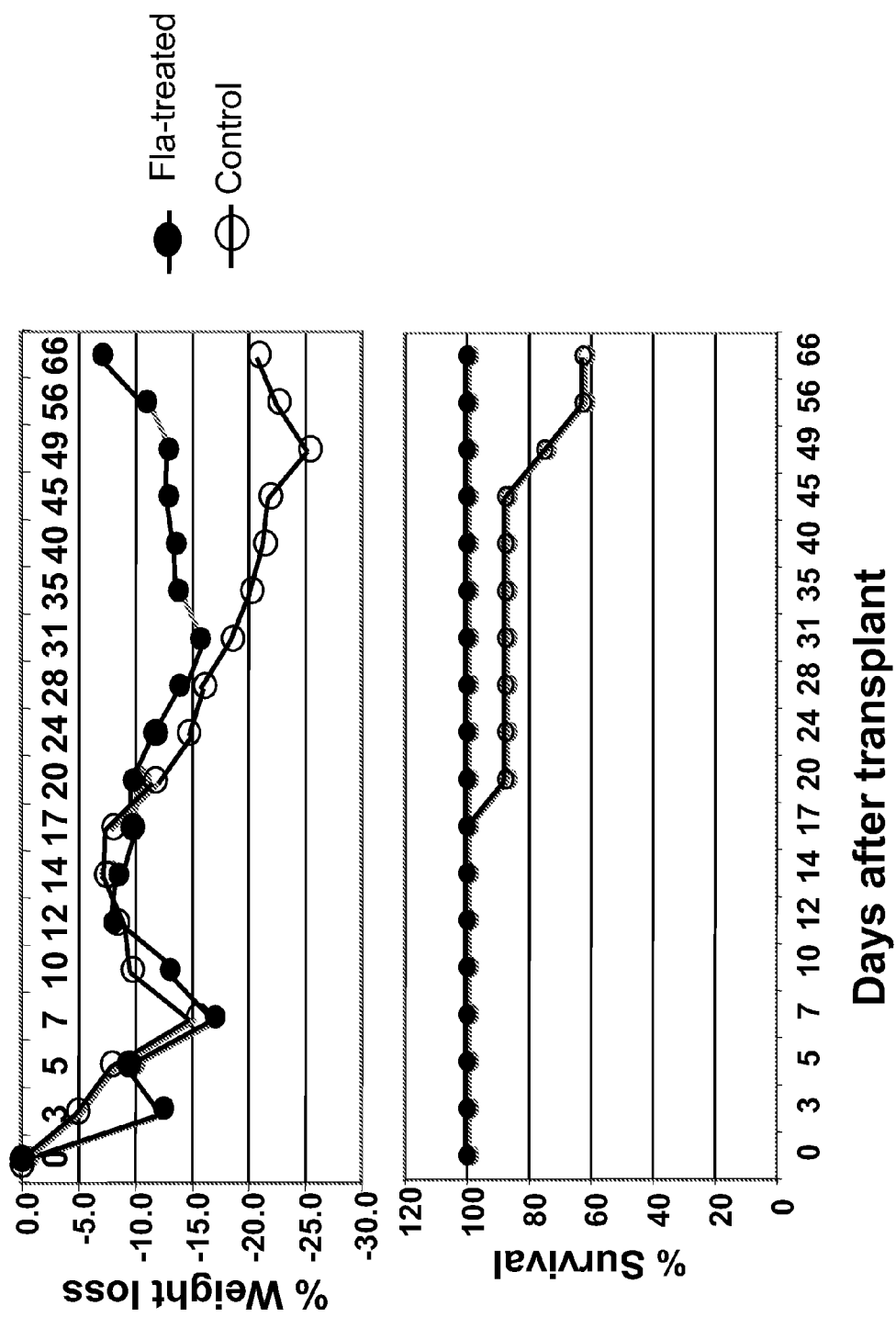
FIG. 3 is a graph showing that flagellin protected bone marrow transplant recipients from GVHD (monitored as weight loss) and the associated mortality. Filled circles indicate the weight loss and mortality of mice treated with flagellin; open circles indicate the weight loss and mortality of control mice.
Figure 4:
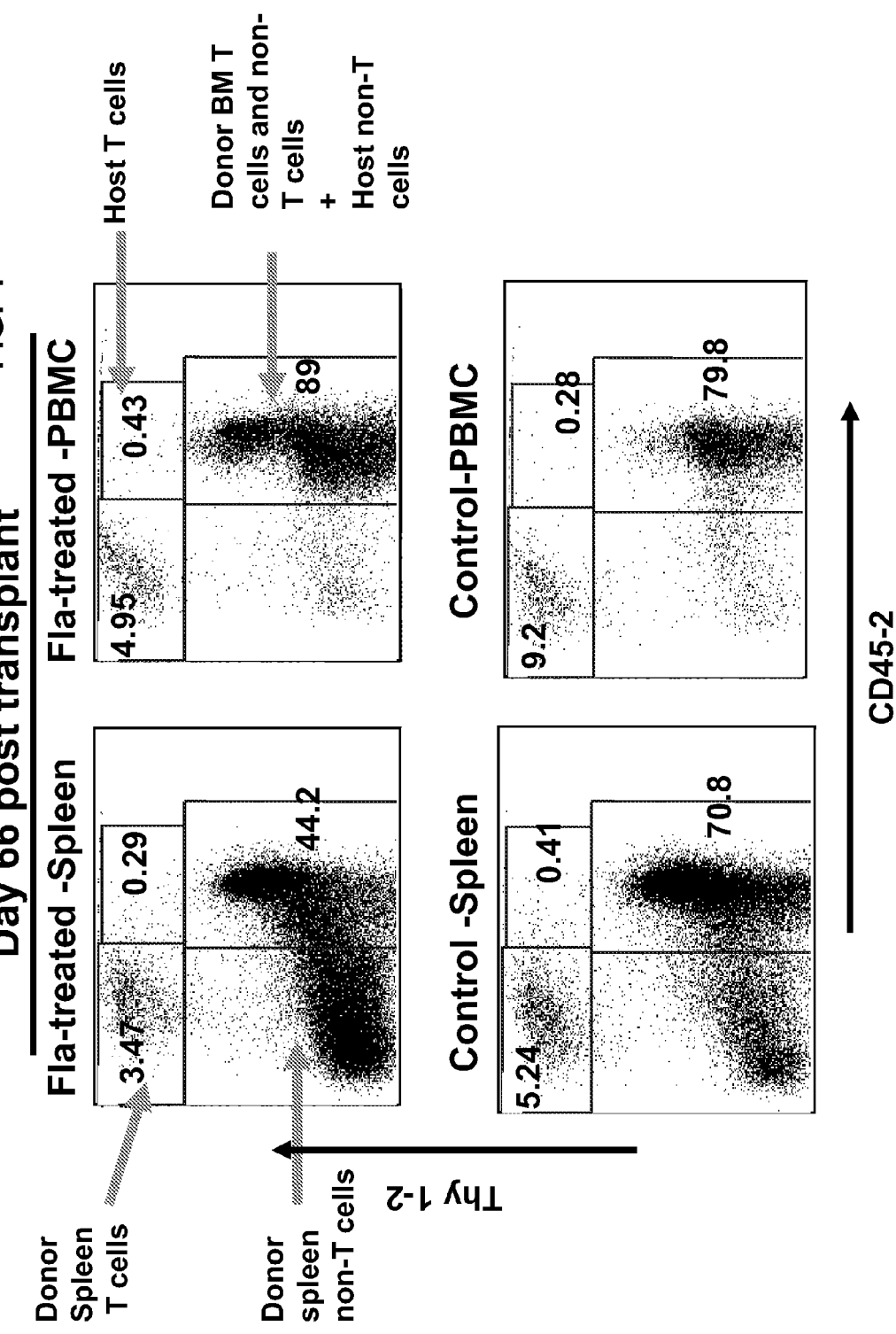
FIG. 4 is a set of plots showing that flagellin facilitated donor T cell chimerism. Peripheral blood mononuclear cells (PBMNC) and splenocytes isolated from HSCT mice were immunostained with antibodies against CD45.2 and Thy1.2 to separate T-cells into those derived from the BMT recipient (Thy 1.2 positive; CD45.2 positive), the BM donor (Thy1.2 negative; CD45.2 positive), or the splenocyte donor (Thy1.2 positive; CD45.2 negative).
Figure 5:
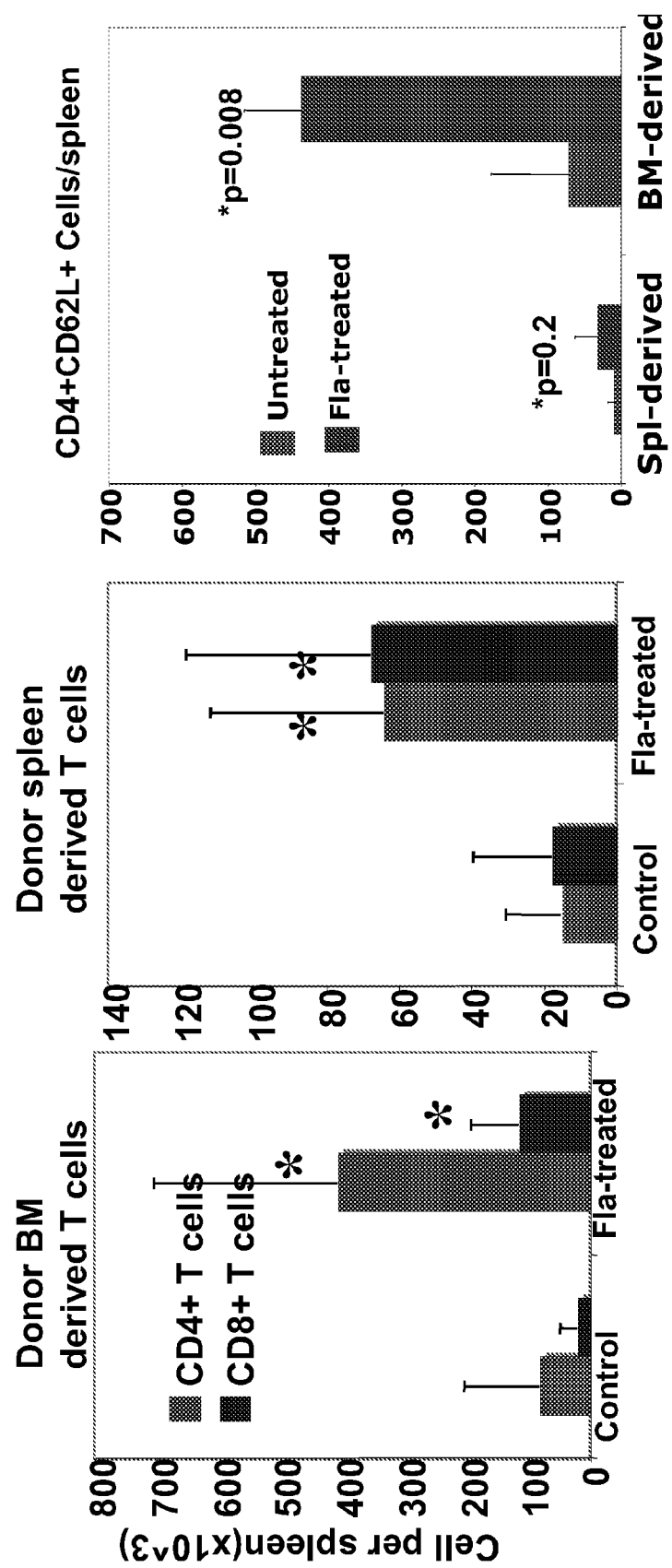
FIG. 5 is a set of bar graphs showing that flagellin facilitated post-HSCT chimerism and that flagellin-treated recipients had higher numbers of donor T cells in the spleen. The methods used in these studies were as described above for FIG. 4.
Figure 6:
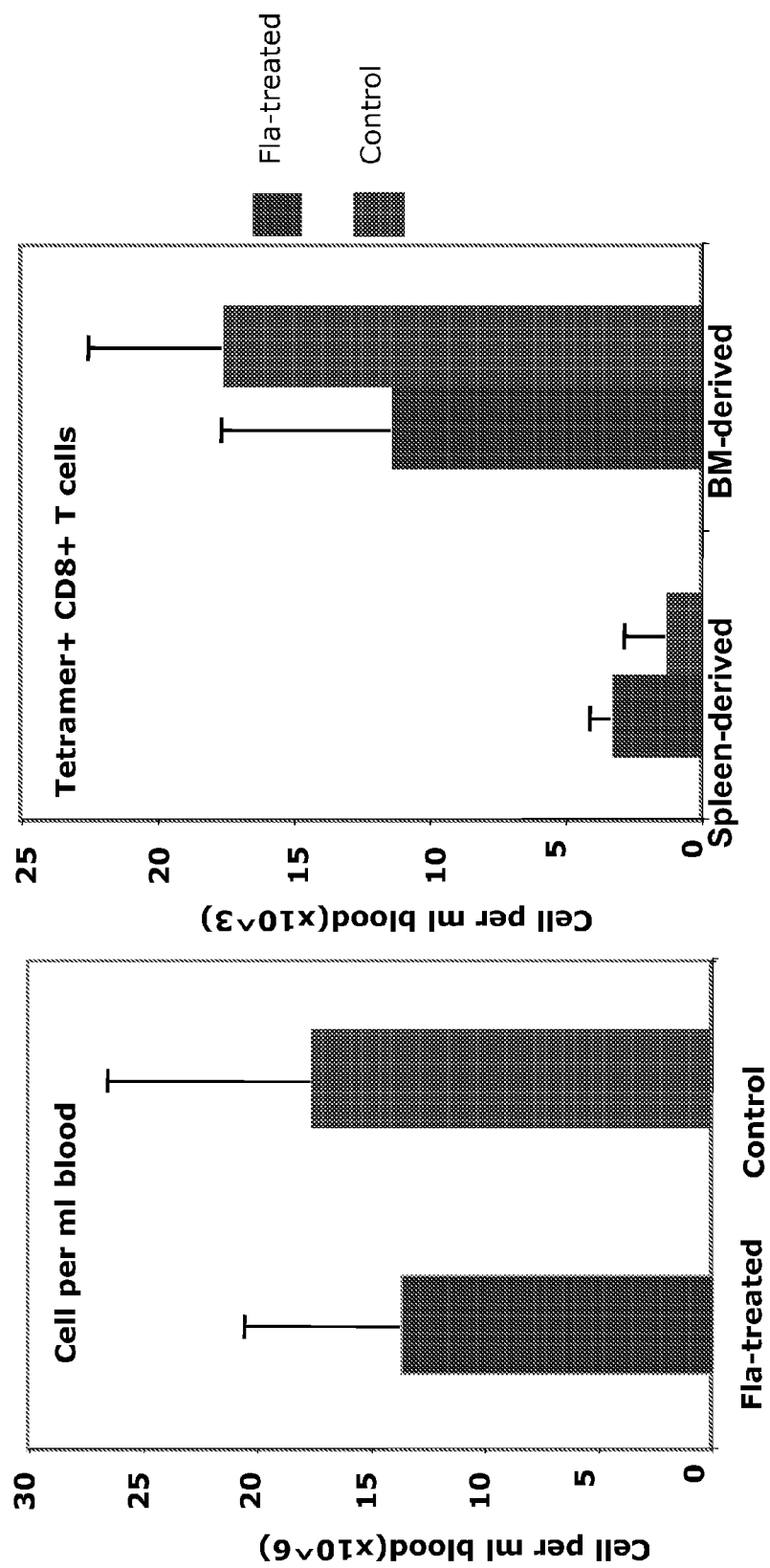
FIG. 6 is a set of bar graphs showing that flagellin-treated recipients responded to a novel CMV vaccine (Lm-MCMV), as demonstrated by the presence of T-cells that stained the PBMNC with an MCMV antigen-specific tetramer on day 7 post vaccination.
Figure 7:
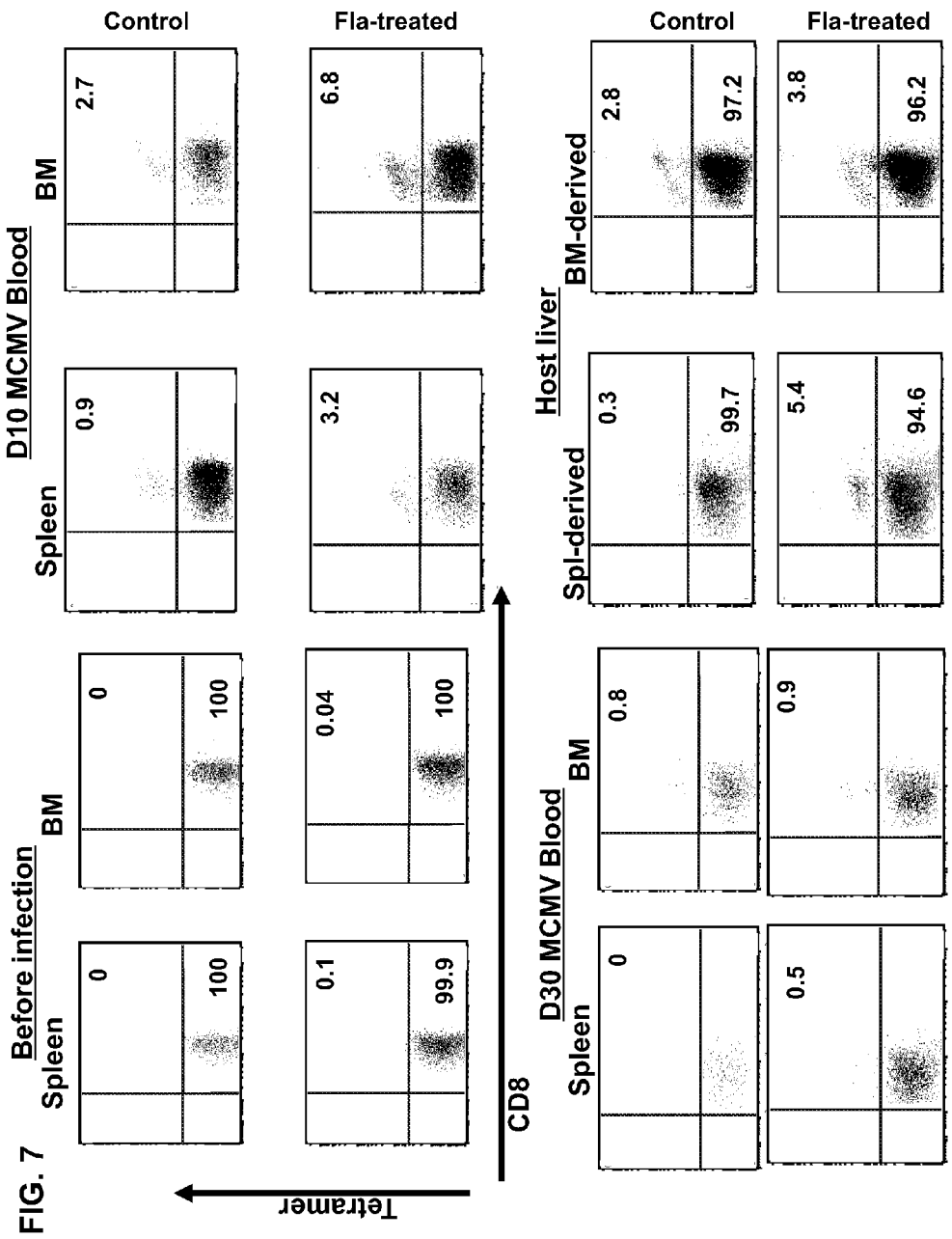
FIG. 7 is a set of plots showing anti-MCMV immunity in Flagellin treated recipients. Flagellin treated and control recipients were bled on day before, and 10 and 30 days post infection. Donor spleen and donor BM-derived Tetramer+ CD8+ were determined by FACS after staining the cells with MCMV peptide specific H-2b tetramer. Both flagellin-treated and control recipients were sacrificed on day 30 post transplantation. Liver lymphocytes were isolated and harvested using Percol gradient concentrations after passing the liver homogenate tissue through a metal mesh. Donor spleen- and BM-derived MCMV peptide specific H-$2^b$ restricted tetramer+ CD8+ T cells were determined by FACS after staining the cells with the similar anti-bodies used for PBMNC.

Flagellin treated recipients that had been transplanted with $5\times10^6$ splenocytes per mouse showed weight loss similar to the untreated group until day 30 post transplant without any mortality. Surprisingly, they started gaining weight and reached their normal values within 100 days post-transplant. On the other hand, the untreated control group had 87% survival at 30 days post transplant and had chronic GVHD (about 25% weight loss) within day 66 post transplant (FIG. 3). Mice were selected from both the treated and untreated groups, and were sacrificed on day 66. PBMC and splenocytes were harvested and analyzed. Both recipient groups (treated with flagellin and untreated) had nearly 100% donor chimerism (FIG. 4) and had similar levels of donor spleen- and BM-derived T cells in their blood. But cell numbers per spleen in the control recipients were significantly decreased compared to the treated recipients (p=0.0006) (FIG. 5). Accordingly, the number of donor spleen and BM-derived CD4+ and CD8+ T cells were found to be significantly decreased but the CD62+CD4+ T cells and CD62L+CD8+ T cells were not significantly different (p=0.129 and p=0.09, respectively). The anti-viral T cell immunity was investigated in these recipients by infecting with murine cytomegalovirus (MCMV) ($5\times10^3$ pfu/mouse) i.p. All mice in the control group with chronic GVHD died within 10 days of infection whereas recipients previously treated with flagellin recovered from MCMV infection and had donor spleen and BM-derived MCMV-peptide specific tetramer+ CD8+ T cells in their blood, spleen and liver on day 10 and 35 days post infection (FIG. 6 and FIG. 7). Increased numbers of CD25+foxp3+ CD4+ regulatory T cells were also measured from their thymus on day 35 post MCMV infection consistent with reduced thymic GvHD in these animals. Moreover, similar doses of flagellin also protected recipients of $10\times10^6$ splenocytes from lethal GVHD until 58 days post transplant, with treated animals showing less than 25% weight loss and only 10% mortality compared with severe acute GVHD and over 30% weight (leading to mandatory euthanasia) among all untreated control recipients (FIG. 8).

Flagellin was effective in treating GVHD and treating an opportunistic infection. Without being bound by theory, agonistic binding of flagellin to TLR5 present in the intestines or other lymphoid organs may reduce the production of biological factor(s), especially inflammatory cytokines, that initiate the generation of allo-reactive T cells and enhance recognition of host alloantigen by the donor T cells. Increased numbers of CD62L+CD4+ T cells and CD62L+CD8+ T cells in the spleen of untreated recipients indicate the presence of GVHD in these mice. In contrast, balanced immune reconstitution in the lymphoid organs of flagellin-treated animals, and the presence of thymic regulatory T cells were likely responsible for the reduced allo-reactivity observed in these transplant recipients. Therefore, the pre-transplant administration of flagellin did not interfere with achievement of 100% donor T-cell chimerism and protected recipients from CMV infection through both donor spleen and BM-derived anti-viral T cells. The absence of clinical GVHD while preserving antigen specific anti-viral immune responses supports the clinical use of flagellin and/or other TLR5 agonists in the setting of allogeneic HSCT. Hence, flagellin can be used in the treatment blood cancer with allogeneic HSCT.

Example 3

Flagellin, a TLR5 Agonist, Controls Differential Expression of CD62L on Donor T Cells that do not Cause GvHD in Allogeneic Hematopoietic Stem Cell Transplantation Previous studies have claimed that CD62L+ T cells are the sole agent to cause GvHD and over 80% of murine naïve donor splenic CD4+ and CD8+ T cells express CD62L. In this study, in vivo differential expression of CD62L was determined on the undivided, dividing and divided donor T cells in flagellin treated allogeneic CFSE (carboxyfluorescein diacetate succinimidyl ester) labeled donor splenocytes comparing the data of CFSE labeled syngeneic HSCT recipients that do not experience GvHD.

For these studies, irradiated (11Gy) CB6F1 (C57BL/6× BALB/c) (H-2b/d, CD45.2+, Thy1.2+) recipient mice received $5\times10^6$ T cell depleted (TCD) bone marrow cells and $5\times10^6$ splenocytes from naïve C57Bl/6 congenic donors (H-2b, CD45.2+, Thy1.1+) and (H-2b, CD45.1+, Thy1.2+) respectively. Fifty microgram (μg) flagellin per recipient was administered intraperitoneally 3 hours before irradiation and 24 hours after allogeneic hematopoietic stem cell transplant (HSCT). CB6F1 recipients that did not receive flagellin were used as control. To investigate the CD62L+ T cell response in vivo, 5 mM CFSE labeled 10×10⁶ donor splenocytes were transplanted in flagellin treated CB6F1 recipients. HSCT CB6F1 recipients without flagellin treatment and C57BL/6 recipients of syngeneic were used as control. Recipients were sacrificed on day 4 post HSCT, splenocytes were harvested and analyzed for CD62L expression on dividing, non-dividing and divided CD4+ and CD8+ T cells by Flow cytometry.

Within day 4 post transplant, in both flagellin treated and untreated recipients of CFSE labeled donor allogeneic splenocytes, CD4+ (treated, 48.9+/−5.5 p=0.00001; untreated 51.6±7.4 p=0.00002) T cells increased significantly compare to CD4+ T cells (20.8±1.7) in recipients of syngeneic splenocytes. Although CD8+ T cells (27.7±2.9) increased significantly (p=0.002) in treated recipients, CD8+ T cells (26.8±7.0) of untreated recipients were not statistically significant (p=0.09) compared to recipients of syngeneic splenocytes. The number of CD62L+CD4+ (treated 28.9±5.3, p=0.000006; untreated, 16.1±11.8, p=0.000005) and CD62L+CD8+ (treated, 23.0±6.6, p=0.00005; untreated, 8.4±5.4, p=0.0000005) T cells decreased significantly in both treated and untreated recipients compare to CD62L+CD4+ and CD62L+CD8+ T cells of syngeneic recipients. The decrease of CD62L+CD4+ T cells in untreated recipients were identical with the treated recipients (p=0.08) but CD62L+CD8+ T cells decreased significantly in untreated recipients compare to treated recipients (p=0.008). Within 4 days post transplant CD62L+CD4+ T cells in treated recipients divided most (52.9±9.7%) followed by untreated recipients (8.5±4.1%) and least in syngeneic recipients (0.6±0.3%). A similar trend was found in CD62L+CD8+ T cells (treated 11.7±4.5%, untreated, 2.4±0.9% and syngeneic 0.2±0.2%). The number of dividing CD62L+CD4+ T cells in untreated recipients (46.3±12.2%) were significantly higher compare to treated recipients (27.7±2.1, p=0.009) and syngeneic recipients (25.7±2.4, p=0.002) but not significant between treated and syngeneic recipients (p=0.2). Whereas the dividing status of CD62L+CD8+ T cells was identical with the syngeneic (66.1±5.7%) and treated (55.6±14.3%) recipients, it was significantly decreased in untreated recipients (33.7+/−10.6) (p=0.0003 and 0.03, respectively). The number of undivided CD62L+CD4+ T cells were the highest in syngeneic (72.3±2.9%) followed by allogeneic (44.3±15.7%) and treated (20.1±7.7%) recipients. However, the numbers of undivided CD62L+CD8+ T cells were the highest in untreated (65.1±8.9%) followed by syngeneic (31.5±5.4%) and treated (28.0±5.0%) recipients.

Thus, agonistic binding of flagellin to LTR5, present in the intestines or other lymphoid organs, differentially controls CD62L+CD4+ and CD62L+CD8+ T cells reactivity in vivo. The differential immune response may be due to 1) reduced production of biological factor(s) essential to generate allo-reactive T cells or directly stimulation of CD62L+CD4+ and CD62L+CD8+ T cells in different activation status other than allo-reactive T cells to prevent GvHD; 2) by controlling GvHD flagellin can maintain a balanced immune reconstitution in lymphoid organs by producing regulatory T cells through their thymus may have strong contribution to control allo-reactivity in flagellin recipients. Therefore, use of flagellin in the treatment blood cancer with allogeneic HSCT without GvHD and toxicity can be used as a therapeutic approach.

Example 4

Prophylactic Use of Flagellin

Method to Boost Immune Reconstitution in Allogeneic HSCT Recipients with Limited GvHD Immunosuppressive drugs limit clinical GvHD but increase relapse and susceptibility to opportunistic infections and also result in drug related toxicities. To develop an alternative approach to control GvHD, the immunomodulatory immune properties of flagellin, a bacterial protein that agonistically binds with TLR5 and protects mice from radiation-induced gut injury, was tested in murine allogeneic bone marrow transplantation (BMT) models.

Established BA.B10 (H-2$^K$)→C57BL/6 (H-2$^b$) MHC mismatched experimental models of allogeneic HSCT were used in which GvHD is a major complication. 50 µg LPS-free purified flagellin in phosphate buffered saline (PBS) or PBS alone were administered intraperitoneally in two doses: 3 hours before fractionated irradiation (5.5Gy×2 fractions) and 1 day post-transplant. Allografts were performed 1 day after irradiation and contained 5 million (M) T-cell depleted bone marrow (BM) cells and 5 M plastic non-adherent splenocytes from naïve BA.B10 donors. The primary end-points was survival; HSCT recipients were monitored twice a day for mortality and GvHD signs and recipients having more than 25% weight loss were sacrificed. Blood, spleen, thymus and BM were collected from surviving mice on day 132 post transplant, live cells counted, and immune phenotypes were analyzed by FACS. The numbers and phenotype of immune cells in organs from flagellin-treated HSCT recipients were compared to the similar immune cells per organs analyzed from a normal B6 mouse having similar age of HSCT recipients.

Flagellin treated recipients had 15% weight-loss and 33% transplant-related death by 132 days post transplant versus severe acute GvHD and 100% early post-transplant mortality among control HSCT recipients that received PBS. Flagellin-treated recipients had 100% donor chimerism with limited clinical signs of GvHD. While total cell numbers per spleen (8.2±5.4M) and thymus (7.1±4.9M) were very low in flagellin-treated recipients compared to normal B6 mice (>100M/organ), the cell numbers isolated from blood (8.9±2.6 M/ml) and BM (104.5±37.4 M) were similar to non-transplanted B6 mice (11.4M/ml blood and 108 M/BM, respectively). BM of flagellin-treated HSCT recipients contained similar numbers of CD4+ T cells (4.6±2.7 M) and CD8+ T cells (2.5±1.4 M) as normal B6 mice (4.03M and 1.3M, respectively). Numbers of naïve and memory CD4+ T-cells in the BM were similar between flagellin-treated and control mice: CD4+CD62L+ (0.7±0.2 versus 0.5M); CD4+CD62L− (3.9±2.5 versus 3.5 M); CD4+ CD44hi (2.8±1.4 versus B6 3.6M); and CD44lo (1.7±1.3 M versus 0.44M). In contrast, flagellin-treated HSCT recipients had more naïve CD8+ T-cells but similar memory CD8+ T-cells in their bone marrow (BM) compared with control mice: CD8+CD62L+(2.6±1.4 versus 1.0M); CD8+CD62L− (1.7±1.2M versus 0.3 M); CD8+CD44hi (0.8±1.1 versus 0.7M); and CD8+ CD44lo (0.7±0.3M versus 0.6 M). The numbers of total CD3+ T cells, NK cells, and lin−CD11b−Sca−1+Ckit+Stem cells in the BM were also similar comparing flagellin-treated recipients with non-transplanted B6 control mice. he number of CD3-B220+ B cells in the BM were lower in flagellin-treated recipients compared to B6 mouse (18.1±3.2M versus 43.1M) as were the numbers of T-cells and B-cells per mL blood of flagellin-treated mice were found lower compared with the blood of normal B6 mouse: 0.8±0.2M T-cells/mL versus 2.1 M/mL; 5.5±2.5M B cells/mL versus 9.1 M/mL. Although the cellularity of the thymus in flagellin-treated animals was very low compared to normal B6 mice, a usual percentage (62.5±10.5%) of thymocytes were of CD4/CD8 double positive, indicating functional thymopoiesis in these recipients.

Thus, flagellin protected allogeneic HSCT recipients from irradiation-induced BM damage and prevented lethal GvHD in a major MHC mis-matched model of GvHD. Flagellin and other TLR5 agonists can be used to prevent or reduce GvHD in allogeneic HSCT recipients.

Example 5

Human Clinical Trial

Patients undergoing allogeneic hematopoietic stem cell transplant receive 1 mg/kg flagellin by sub-cutaneous injection 1 day prior to treatment with myeloablative doses of chemo/radiotherapy, typically 12 Gy total body irradiation delivered as six fractions over three consecutive days followed by 120 mg/kg cyclophosphamide delivered by intravenous infusion over two consecutive days. Allogeneic donor stem cells or bone marrow cells containing at least $1 \times 10^6$ CD34+ cells./kg and up to $30 \times 10^6$ CD34+ cells/kg, typically $2 \times 10^6$ to $10 \times 10^6$ are infused intravenously one day after completing the conditioning regimen and a second dose of 1 mg/kg flagellin is administered one day following the transplant. Patients receive standard pharmacological immunoprophylaxis against graft versus host disease with the continuous intravenous administration of Pmgaf, and intravenous injections of 10 mg/m$^6$ methotrexate on day 1, 3, 6, and 11 post-transplant. Patients are monitored for stem cell engraftment and receive standard supportive care including blood transfusions and the administration of antibiotics.

It will be apparent that the precise details of the methods or compositions described may be varied or modified without departing from the spirit of the described invention. We claim all such modifications and variations that fall within the scope and spirit of the claims below.

The invention claimed is:

1. A method of treating or preventing graft versus host disease in a subject, comprising: selecting a subject in need of treatment for graft versus host disease; and administering to the subject a therapeutically effective amount of a pharmaceutical composition comprising a flagellin polypeptide or fragment thereof able to activate the toll-Like Receptor 5 (TLR5) pathway, thereby treating or preventing graft versus host disease in the subject.

2. The method of, claim 1, wherein the subject in need of treatment for graft versus host disease has or will receive an allogeneic bone marrow or hematopoietic stem cell transplant.

3. The method of, claim 1, wherein the flagellin polypeptide is administered concurrently with an allogeneic bone marrow or hematopoietic stem cell transplant.

4. The method of, claim 1, wherein the flagellin polypeptide is administered following an allogeneic bone marrow or hematopoietic stem cell transplant.

5. The method of, claim 1, wherein the flagellin polypeptide is administered prior to an allogeneic bone marrow or hematopoietic stem cell transplant.

6. The method of claim 1, wherein the flagellin polypeptide comprises the N-terminal constant region and the C-terminal constant region.

7. The method of claim 1, wherein the flagellin polypeptide-comprises at least 100 amino acids of the N-terminal amino acid sequence and at least 100 C-terminal amino acids of Salmonella typhimurium flagellin containing at most 20 amino acid substitutions.

8. The method of claim 7, wherein the N-terminal amino acid sequence comprises the amino acid sequence of SEQ ID NO:3.

9. The method of claim 7, wherein the C-terminal amino acid sequence comprises the amino acid sequence of SEQ ID NO:4.

10. The method of claim 1, wherein the flagellin polypeptide comprises amino acids 78-129, amino acids 135-173, amino acids 394-444, or any combination thereof from SEQ ID NO:2.

11. The method of claim 1, wherein the subject is human.

12. The method of claim 1, wherein the flagellin polypeptide comprises the amino acid sequence of SEQ ID NO:1 or 2.

13. The method of claim 1, wherein the flagellin polypeptide is CBLB502.

14. A method for reducing susceptibility to an opportunistic infection in a subject who is a bone marrow transplant recipient, comprising selecting a subject who has had an allogeneic bone marrow or hematopoietic stem cell transplant; and administering to the subject a therapeutically effective amount of a pharmaceutical composition comprising a flagellin polypeptide or fragment thereof able to activate the toll-Like Receptor 5 (TLR5) pathway; administering to the subject an effective amount of an antigen of the opportunistic infection; wherein the pharmaceutical composition and the antigen reduce the susceptibility to the opportunistic infection in the subject.

* * * * *

SEQUENCE LISTING

```
<160> NUMBER OF SEQ ID NOS: 4

<210> SEQ ID NO 1
<211> LENGTH: 585
<212> TYPE: PRT
<213> ORGANISM: Escherichia coli

<400> SEQUENCE: 1

Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ala Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Ile Arg Glu Leu Thr
                85                  90                  95

Val Gln Ala Thr Thr Gly Thr Asn Ser Asp Ser Asp Leu Asp Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Leu Ala Lys Asp Gly Ser Met
    130                 135                 140

Lys Ile Gln Val Gly Ala Asn Asp Gly Glu Thr Ile Thr Ile Asp Leu
145                 150                 155                 160

Lys Lys Ile Asp Ser Asp Thr Leu Gly Leu Asn Gly Phe Asn Val Asn
                165                 170                 175

Gly Lys Gly Thr Ile Thr Asn Lys Ala Ala Thr Val Ser Asp Leu Thr
            180                 185                 190

Ser Ala Gly Ala Lys Leu Asn Thr Thr Thr Gly Leu Tyr Asp Leu Lys
        195                 200                 205

Thr Glu Asn Thr Leu Leu Thr Thr Asp Ala Ala Phe Asp Lys Leu Gly
    210                 215                 220

Asn Gly Asp Lys Val Thr Val Gly Gly Val Asp Tyr Thr Tyr Asn Ala
225                 230                 235                 240

Lys Ser Gly Asp Phe Thr Thr Thr Lys Ser Thr Ala Gly Thr Gly Val
                245                 250                 255
```

Asp Ala Ala Ala Gln Ala Ala Asp Ser Ala Ser Lys Arg Asp Ala Leu
                260                 265                 270

Ala Ala Thr Leu His Ala Asp Val Gly Lys Ser Val Asn Gly Ser Tyr
            275                 280                 285

Thr Thr Lys Asp Gly Thr Val Ser Phe Glu Thr Asp Ser Ala Gly Asn
        290                 295                 300

Ile Thr Ile Gly Gly Ser Gln Ala Tyr Val Asp Asp Ala Gly Asn Leu
305                 310                 315                 320

Thr Thr Asn Asn Ala Gly Ser Ala Ala Lys Ala Asp Met Lys Ala Leu
                325                 330                 335

Leu Lys Ala Ala Ser Glu Gly Ser Asp Gly Ala Ser Leu Thr Phe Asn
            340                 345                 350

Gly Thr Glu Tyr Thr Ile Ala Lys Ala Thr Pro Ala Thr Thr Thr Pro
        355                 360                 365

Val Ala Pro Leu Ile Pro Gly Gly Ile Thr Tyr Gln Ala Thr Val Ser
    370                 375                 380

Lys Asp Val Val Leu Ser Glu Thr Lys Ala Ala Ala Thr Ser Ser
385                 390                 395                 400

Ile Thr Phe Asn Ser Gly Val Leu Ser Lys Thr Ile Gly Phe Thr Ala
                405                 410                 415

Gly Glu Ser Ser Asp Ala Ala Lys Ser Tyr Val Asp Asp Lys Gly Gly
            420                 425                 430

Ile Thr Asn Val Ala Asp Tyr Thr Val Ser Tyr Ser Val Asn Lys Asp
        435                 440                 445

Asn Gly Ser Val Thr Val Ala Gly Tyr Ala Ser Ala Thr Asp Thr Asn
    450                 455                 460

Lys Asp Tyr Ala Pro Ala Ile Gly Thr Ala Val Asn Val Asn Ser Ala
465                 470                 475                 480

Gly Lys Ile Thr Thr Glu Thr Thr Ser Ala Gly Ser Ala Thr Thr Asn
                485                 490                 495

Pro Leu Ala Ala Leu Asp Asp Ala Ile Ser Ser Ile Asp Lys Phe Arg
            500                 505                 510

Ser Ser Leu Gly Ala Ile Gln Asn Arg Leu Asp Ser Ala Val Thr Asn
        515                 520                 525

Leu Asn Asn Thr Thr Thr Asn Leu Ser Glu Ala Gln Ser Arg Ile Gln
    530                 535                 540

Asp Ala Asp Tyr Ala Thr Glu Val Ser Asn Met Ser Lys Ala Gln Ile
545                 550                 555                 560

Ile Gln Gln Ala Gly Asn Ser Val Leu Ala Lys Ala Asn Gln Val Pro
                565                 570                 575

Gln Gln Val Leu Ser Leu Leu Gln Gly
            580                 585

<210> SEQ ID NO 2
<211> LENGTH: 506
<212> TYPE: PRT
<213> ORGANISM: Salmonella muenchen

<400> SEQUENCE: 2

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

-continued

```
Ala Ile Ala Asn Arg Phe Thr Ala Asn Ile Lys Gly Leu Thr Gln Ala
 50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Leu Gln Arg Val Arg Glu Leu Ala
                 85                  90                  95

Val Gln Ser Ala Asn Ser Thr Asn Ser Gln Ser Asp Leu Asp Ser Ile
                100                 105                 110

Gln Ala Glu Ile Thr Gln Arg Leu Asn Glu Ile Asp Arg Val Ser Gly
                115                 120                 125

Gln Thr Gln Phe Asn Gly Val Lys Val Leu Ala Gln Asp Asn Thr Leu
130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val Gln
                165                 170                 175

Lys Ala Tyr Asp Val Lys Asp Thr Ala Val Thr Thr Lys Ala Tyr Ala
                180                 185                 190

Asn Asn Gly Thr Thr Leu Asp Val Ser Gly Leu Asp Asp Ala Ala Ile
                195                 200                 205

Lys Ala Ala Thr Gly Gly Thr Asn Gly Thr Ala Ser Val Thr Gly Gly
210                 215                 220

Ala Val Lys Phe Asp Ala Asp Asn Asn Lys Tyr Phe Val Thr Ile Gly
225                 230                 235                 240

Gly Phe Thr Gly Ala Asp Ala Ala Lys Asn Gly Asp Tyr Glu Val Asn
                245                 250                 255

Val Ala Thr Asp Gly Thr Val Thr Leu Ala Ala Gly Ala Thr Lys Thr
                260                 265                 270

Thr Met Pro Ala Gly Ala Thr Thr Lys Thr Glu Val Gln Glu Leu Lys
                275                 280                 285

Asp Thr Pro Ala Val Val Ser Ala Asp Ala Lys Asn Ala Leu Ile Ala
                290                 295                 300

Gly Gly Val Asp Ala Thr Asp Ala Asn Gly Ala Glu Leu Val Lys Met
305                 310                 315                 320

Ser Tyr Thr Asp Lys Asn Gly Lys Thr Ile Glu Gly Gly Tyr Ala Leu
                325                 330                 335

Lys Ala Gly Asp Lys Tyr Tyr Ala Ala Asp Tyr Asp Glu Ala Thr Gly
                340                 345                 350

Ala Ile Lys Ala Lys Thr Thr Ser Tyr Thr Ala Ala Asp Gly Thr Thr
                355                 360                 365

Lys Thr Ala Ala Asn Gln Leu Gly Gly Val Asp Gly Lys Thr Glu Val
                370                 375                 380

Val Thr Ile Asp Gly Lys Thr Tyr Asn Ala Ser Lys Ala Ala Gly His
385                 390                 395                 400

Asp Phe Lys Ala Gln Pro Glu Leu Ala Glu Ala Ala Lys Thr Thr
                405                 410                 415

Glu Asn Pro Leu Gln Lys Ile Asp Ala Ala Leu Ala Gln Val Asp Ala
                420                 425                 430

Leu Arg Ser Asp Leu Gly Ala Val Gln Asn Arg Phe Asn Ser Ala Ile
                435                 440                 445

Thr Asn Leu Gly Asn Thr Val Asn Asn Leu Ser Glu Ala Arg Ser Arg
                450                 455                 460

Ile Glu Asp Ser Asp Tyr Ala Thr Glu Val Ser Asn Met Ser Arg Ala
```

-continued

```
            465                 470                 475                 480
Gln Ile Leu Gln Gln Ala Gly Thr Ser Val Leu Ala Gln Ala Asn Gln
                        485                 490                 495

Val Pro Gln Asn Val Leu Ser Leu Leu Arg
                500                 505

<210> SEQ ID NO 3
<211> LENGTH: 5
<212> TYPE: PRT
<213> ORGANISM: Salmonella dublin

<400> SEQUENCE: 3

Arg Ile Asn Ser Ala
1               5

<210> SEQ ID NO 4
<211> LENGTH: 12
<212> TYPE: PRT
<213> ORGANISM: Salmonella muenchen

<400> SEQUENCE: 4

Gly Ala Val Gln Asn Arg Phe Asn Ser Ala Ile Thr
1               5                   10
```